United States Patent
Hofmeister et al.

(10) Patent No.: US 7,228,191 B2
(45) Date of Patent: Jun. 5, 2007

(54) METHOD AND APPARATUS FOR CONSTRUCTING CROWNS, BRIDGES AND IMPLANTS FOR DENTAL USE

(75) Inventors: Andrew Hofmeister, Chanhassen, MN (US); James Ledin, Chanhassen, MN (US); Bob Isaacson, Edina, MN (US); Bruce Hultgren, Victoria, MN (US); Mike Marshall, Savage, MN (US)

(73) Assignee: Geodigm Corporation, Chanhassen, MN (US)

( * ) Notice: Subject to any disclaimer, the term of this patent is extended or adjusted under 35 U.S.C. 154(b) by 177 days.

(21) Appl. No.: 10/429,288

(22) Filed: May 2, 2003

(65) Prior Publication Data

US 2004/0220691 A1    Nov. 4, 2004

(51) Int. Cl.
*G06F 19/00* (2006.01)
*A61C 5/10* (2006.01)

(52) U.S. Cl. .................. 700/98; 700/117; 700/119; 433/218; 433/223

(58) Field of Classification Search .................. 700/98, 700/182, 117, 118, 119, 120; 433/6, 24, 433/213, 29, 183; 382/154
See application file for complete search history.

(56) References Cited

U.S. PATENT DOCUMENTS

| | | | |
|---|---|---|---|
| 2,194,790 A | 3/1940 | Glück | 32/12 |
| 3,807,862 A | 4/1974 | Hatzenbuhler | |
| 4,273,580 A | 6/1981 | Shoher et al. | 75/165 |
| 4,411,626 A | 10/1983 | Becker et al. | |
| 4,611,288 A | 9/1986 | Duret et al. | |
| 4,663,720 A | 5/1987 | Duret et al. | |
| 4,742,464 A | 5/1988 | Duret et al. | |
| 4,850,873 A | 7/1989 | Lazzara et al. | 433/220 |
| 4,869,666 A | 9/1989 | Talass | |
| 4,952,149 A | 8/1990 | Duret et al. | |
| 5,011,405 A | 4/1991 | Lemchen | |
| 5,092,022 A | 3/1992 | Duret | |
| 5,139,419 A | 8/1992 | Andreiko et al. | |
| 5,232,361 A | 8/1993 | Sachdeva et al. | |
| 5,237,998 A | 8/1993 | Duret et al. | |

(Continued)

FOREIGN PATENT DOCUMENTS

EP    0 316 106 A1    5/1989

(Continued)

OTHER PUBLICATIONS

Lewis, J., "Software beefs up tractor radiator-guard mount," *Design News*, vol. 54, No. 4, pp. 87-88 (Feb. 15, 1999) (1 page abstract).

(Continued)

*Primary Examiner*—Leo Picard
*Assistant Examiner*—Charles Kasenge
(74) *Attorney, Agent, or Firm*—Merchant & Gould P.C.

(57) ABSTRACT

A method, apparatus, and article of manufacture is disclosed for providing a dental crowns using electronic models, and more particularly to a method, apparatus, and article of manufacture for creating dental crowns using a lost-wax manufacturing process from electronic model files corresponding to patient teeth impressions and corresponding electronic models for tooth crowns. The system and method permit the electronic generation and specification of crown, bridge, and implant dental appliances that may be specified in an industry standard file specification. This specification is utilized in a rapid prototyping process to generate a wax impression for the appliance that may then be fabricated using standard lost-wax fabrication techniques.

18 Claims, 24 Drawing Sheets

U.S. PATENT DOCUMENTS

| | | | |
|---|---|---|---|
| 5,257,203 | A | 10/1993 | Riley et al. |
| 5,338,198 | A | 8/1994 | Wu et al. |
| 5,368,478 | A | 11/1994 | Andreiko et al. |
| 5,431,562 | A | 7/1995 | Andreiko et al. |
| 5,447,432 | A | 9/1995 | Andreiko et al. |
| 5,454,717 | A | 10/1995 | Andreiko et al. |
| RE35,169 | E | 3/1996 | Lemchen et al. |
| 5,518,397 | A | 5/1996 | Andreiko et al. |
| 5,588,832 | A | 12/1996 | Farzin-Nia |
| 5,683,243 | A | 11/1997 | Andreiko et al. |
| 5,690,490 | A | 11/1997 | Cannon et al. |
| 5,725,376 | A | 3/1998 | Poirier |
| 6,015,289 | A | 1/2000 | Andreiko et al. |
| 6,042,374 | A | 3/2000 | Farzin-Nia et al. |
| 6,049,743 | A | 4/2000 | Baba |
| RE36,863 | E | 9/2000 | Snyder |
| 6,152,731 | A | 11/2000 | Jordan et al. |
| 6,174,168 | B1 | 1/2001 | Dehoff et al. ............ 433/202.1 |
| 6,177,034 | B1 | 1/2001 | Ferrone |
| 6,217,334 | B1 | 4/2001 | Hultgren |
| 6,227,850 | B1* | 5/2001 | Chishti et al. ................ 433/24 |
| 6,287,121 | B1 | 9/2001 | Guiot et al. |
| 6,322,728 | B1 | 11/2001 | Brodkin et al. |
| 6,354,836 | B1 | 3/2002 | Panzera et al. |
| 6,371,761 | B1* | 4/2002 | Cheang et al. ................ 433/24 |
| 6,398,554 | B1 | 6/2002 | Perot et al. |
| 6,409,504 | B1* | 6/2002 | Jones et al. ................... 433/24 |
| 6,460,594 | B1 | 10/2002 | Lam |
| 6,463,344 | B1* | 10/2002 | Pavloskaia et al. ........... 700/98 |
| 6,506,054 | B2 | 1/2003 | Shoher et al. |
| 6,532,299 | B1 | 3/2003 | Sachdeva et al. |
| 6,568,936 | B2 | 5/2003 | MacDougald et al. |
| 6,648,640 | B2* | 11/2003 | Rubbert et al. ................ 433/24 |
| 6,648,645 | B1* | 11/2003 | MacDougald et al. ...... 433/223 |
| 6,667,112 | B2 | 12/2003 | Prasad et al. |
| 6,691,764 | B2 | 2/2004 | Embert et al. |
| 6,835,066 | B2 | 12/2004 | Iiyama et al. |
| 6,915,178 | B2 | 7/2005 | O'Brien et al. |
| 2002/0015934 | A1* | 2/2002 | Rubbert et al. ................ 433/29 |
| 2002/0110786 | A1 | 8/2002 | Dillier |
| 2004/0137408 | A1 | 7/2004 | Embert et al. |
| 2004/0204787 | A1 | 10/2004 | Kopelman et al. .......... 700/182 |
| 2004/0220691 | A1 | 11/2004 | Hofmeister et al. .......... 700/98 |
| 2005/0251281 | A1 | 11/2005 | O'Brien et al. |

FOREIGN PATENT DOCUMENTS

| | | |
|---|---|---|
| EP | 0 502 227 B1 | 11/1996 |
| FR | 2 593 384 A1 | 1/1986 |
| JP | 5049651 A | 3/1993 |
| WO | WO 94/10935 | 5/1994 |
| WO | WO 02/19940 A1 | 3/2002 |
| WO | WO 02/076327 A1 | 10/2002 |

OTHER PUBLICATIONS

Rotert, V., "How one rapid prototyping method is able to eliminate tooling for investment casting," *Proceedings of the 45th Annual Technical Meeting and Exhibition Investment Casting Institute*, Atlanta, Georgia (1997) (1 page abstract).

Weeden, B. et al., "Alternate methods for custom implant production utilizing a combination of rapid prototyping technology and conventional investment casting," *Proceedings of the 1996 15th Southern Biomedical Engineering Conference*, Dayton, Ohio (1996) (1 page abstract).

Wirtz, H. et al., "Investment casting shells in 1 day using selective laser sintering (SLS)," *Proceedings of the 24th BICTA Conference on Investment Casting*, Oxford, GB (1999) (1 page abstract).

Wu, M. et al., "Application of rapid prototyping and numerical simulation in titanium dental castings," *Computer Assisted Surgery & Rapid Prototyping in Medicine*, 5th Int. Workshop (1999) (1 page abstract).

\* cited by examiner

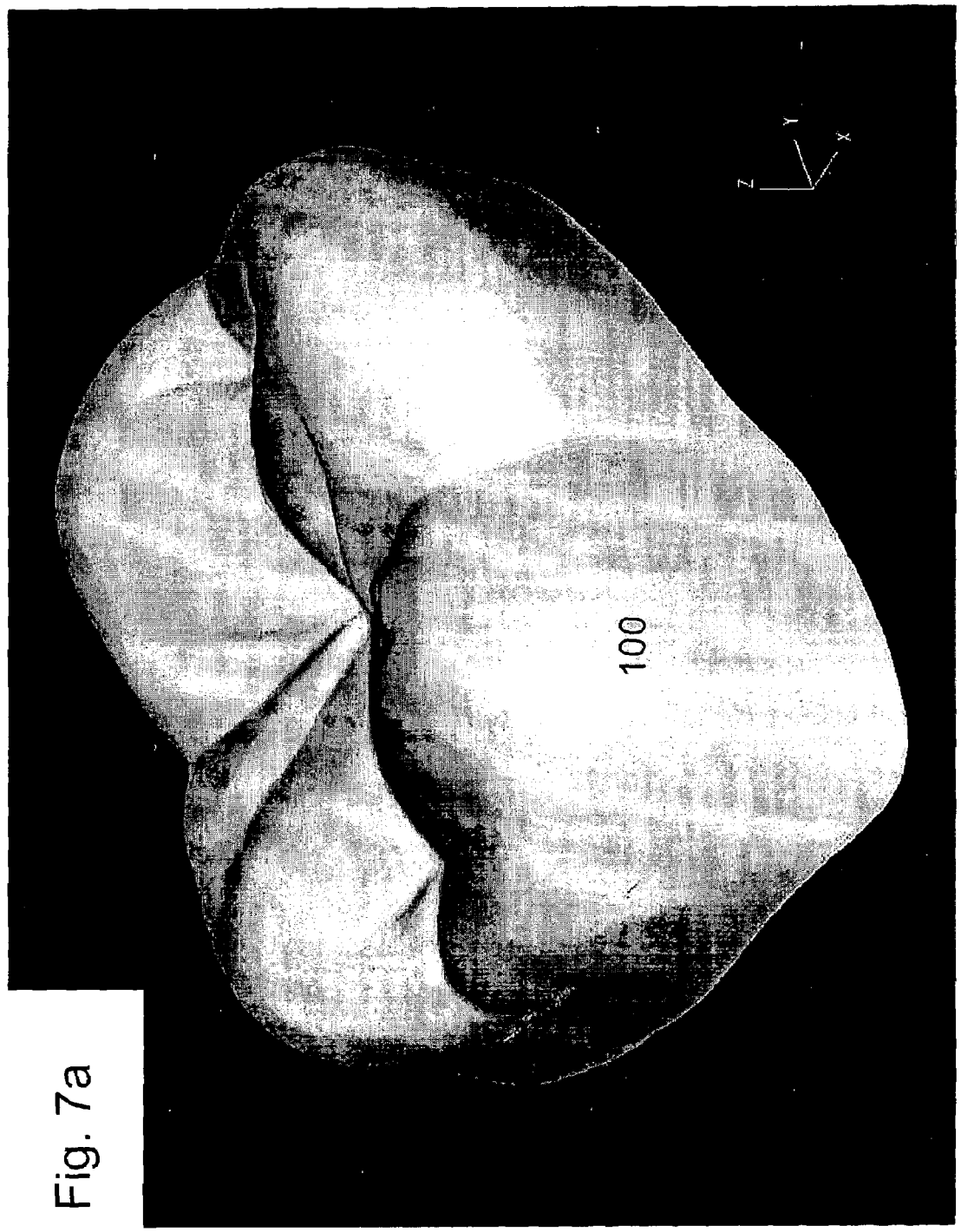

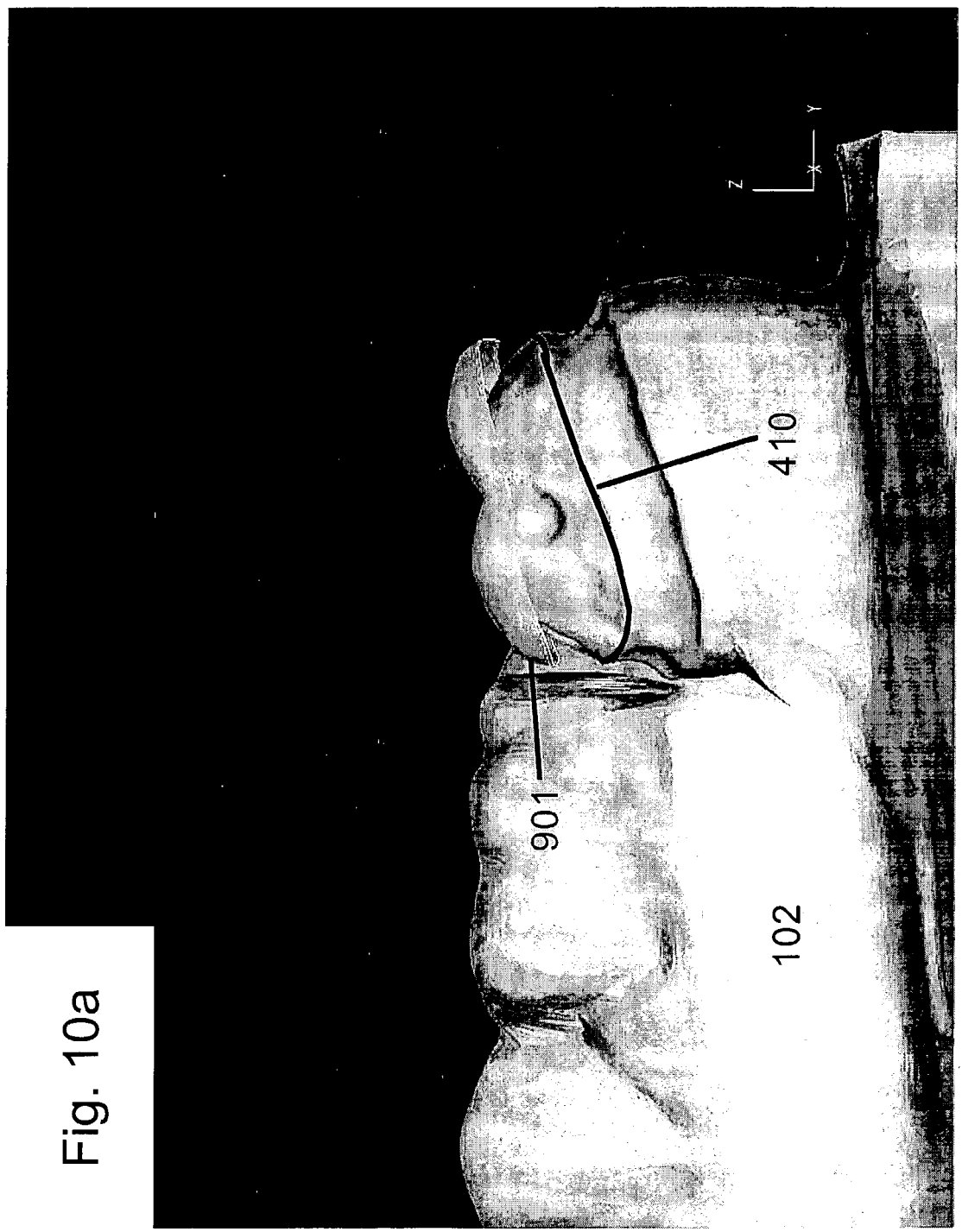

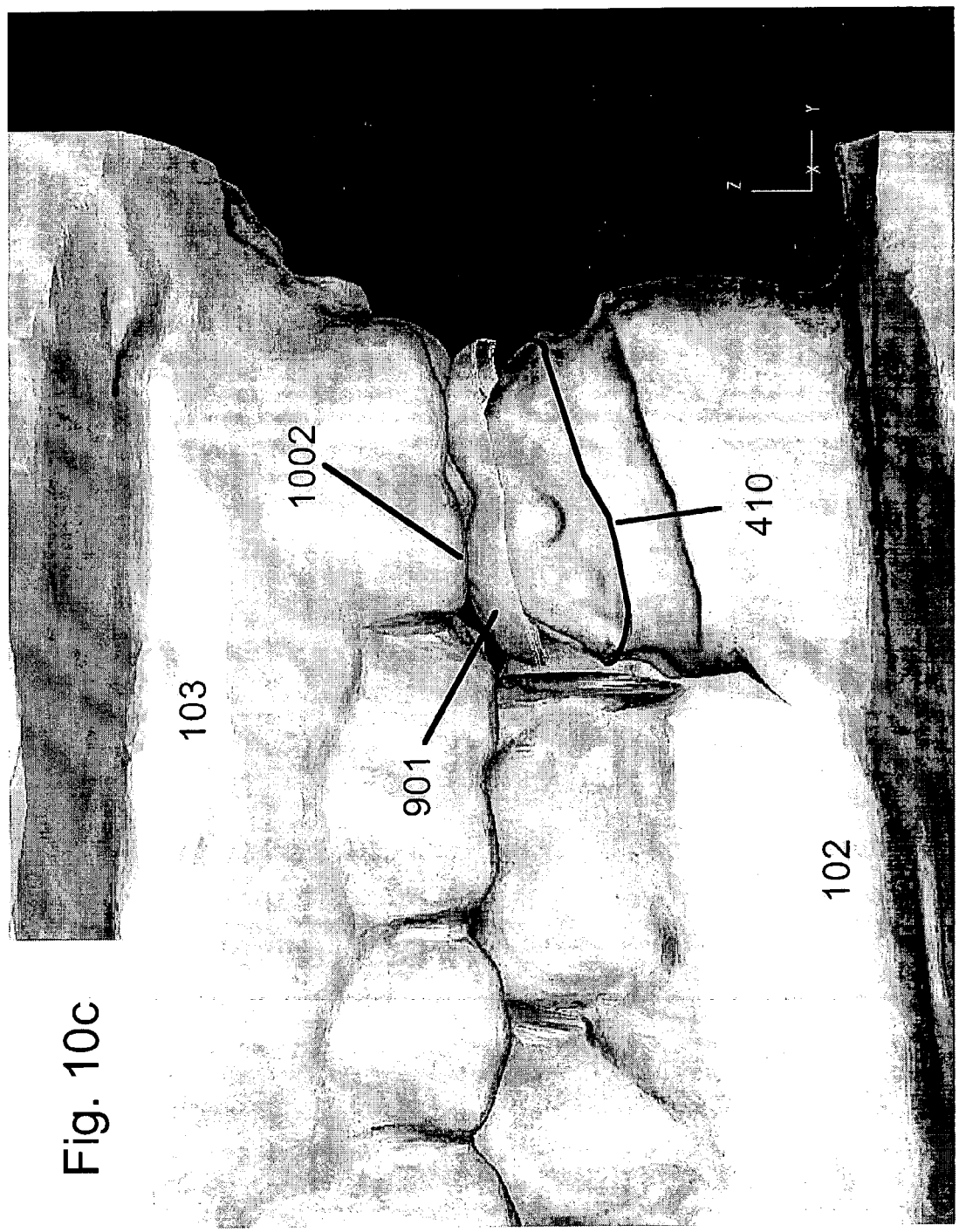

METHOD AND APPARATUS FOR CONSTRUCTING CROWNS, BRIDGES AND IMPLANTS FOR DENTAL USE

TECHNICAL FIELD

This application relates in general to a method, apparatus, and article of manufacture for providing a dental crowns using electronic models, and more particularly to a method, apparatus, and article of manufacture for creating dental crowns using a lost-wax manufacturing process from electronic model files corresponding to patient teeth impressions and corresponding electronic models for tooth crowns.

BACKGROUND OF THE INVENTION

Recently, computing systems have increased in computational power to permit the development of processing systems to generate, manipulate and utilize electronic mesh-based models for physical objects having sufficient spatial resolution to permit the replacement of physical models in many applications. The dental industry has for a long time utilized physical models to observe the interaction of patient's teeth with opposing teeth as well as the introduction of dental appliances such as crowns, bridges and implants (CBI) into a patient's mouth. These models are utilized to select, size and orient the CBI devices before the devices are placed into a patient's mouth. This use of physical models is expensive as it requires the creation of multiple models as a patient's treatment plan progresses. In addition, these physical models must be stored for later retrieval.

Computer based systems that allow the creation and use of electronic models of these impressions of teeth have been developed over time. Examples of such systems are described in U.S. Provisional Patent Application entitled, "METHOD AND APPARATUS FOR COMPUTER GENERATION OF ELECTRONIC MODEL IMAGES", Ser. No. 60/351,270 filed Jan. 22, 2002, now U.S. patent application entitled, "METHOD AND APPARATUS FOR COMPUTER GENERATION OF ELECTRONIC MODEL IMAGES", Ser. No. 10/350,302, filed Jan. 22, 2003; and U.S. Provisional Patent Application entitled, "METHOD AND APPARATUS FOR AUTOMATICALLY DETERMINING THE LOCATION OF INDIVIDUAL TEETH WITHIN ELECTRONIC MODEL IMAGES", Ser. No. 60/351,271, filed Jan. 22, 2002, now U.S. patent application entitled, "METHOD AND APPARATUS FOR AUTOMATICALLY DETERMINING THE LOCATION OF INDIVIDUAL TEETH WITHIN ELECTRONIC MODEL IMAGES", Ser. No. 10/350,304, filed Jan. 22, 2003. These applications are commonly assigned with the instant application and are incorporated by reference herein. These prior systems generated the electronic models and systems used to permit dentists to use the models in place of the physical models. The prior systems permit the manipulation of teeth within the model are part of designing a treatment plan for a patient.

These earlier systems, however, do not utilize dental CBI appliances in the electronic model processing. If an electronic model for such a CBI appliance is constructed electronically to fit a prep site found in an electronic model for a patient, a custom CBI appliance may be constructed that more accurately matches the patient's mouth. The entire manipulation of the CBI appliance may be performed electronically to obtain a more optimum dental solution for a patient with a resulting CBI appliance device created using a standard lost-wax manufacturing process based upon an electronic model generated for the CBI appliance. The present invention addresses the above limitations of prior dental electronic modeling systems.

SUMMARY OF THE INVENTION

In accordance with the present invention, the above and other problems are solved by providing a method, apparatus, and article of manufacture for providing a dental crowns using electronic models, and more particularly to a method, apparatus, and article of manufacture for creating dental crowns using a lost-wax manufacturing process from electronic model files corresponding to patient teeth impressions and corresponding electronic models for tooth crowns.

The great utility of the invention is that the system and method permit the electronic generation and specification of crown, bridge, and implant dental appliances that may be specified in an industry standard file specification. This specification is utilized in a rapid prototyping process to generate a wax impression for the appliance that may then be fabricated using standard lost-wax fabrication techniques.

These and various other features as well as advantages, which characterize the present invention, will be apparent from a reading of the following detailed description and a review of the associated drawings.

BRIEF DESCRIPTION OF THE DRAWINGS

Referring now to the drawings in which like reference numbers represent corresponding parts throughout:

FIGS. 7a–7d illustrate various views of an electronic model for a dental crown constructed according to an embodiment of the present invention.

FIGS. 10a–10c illustrate correcting placement and orientation of a dental crown upon a prep site using previously selected match points according to an embodiment of the present invention.

DETAILED DESCRIPTION

This application relates in general to a method, apparatus, and article of manufacture for creating dental crowns using a lost-wax manufacturing process from electronic model files corresponding to patient teeth impressions and corresponding electronic models for tooth crowns, bridges and implant devices.

Figure 1:
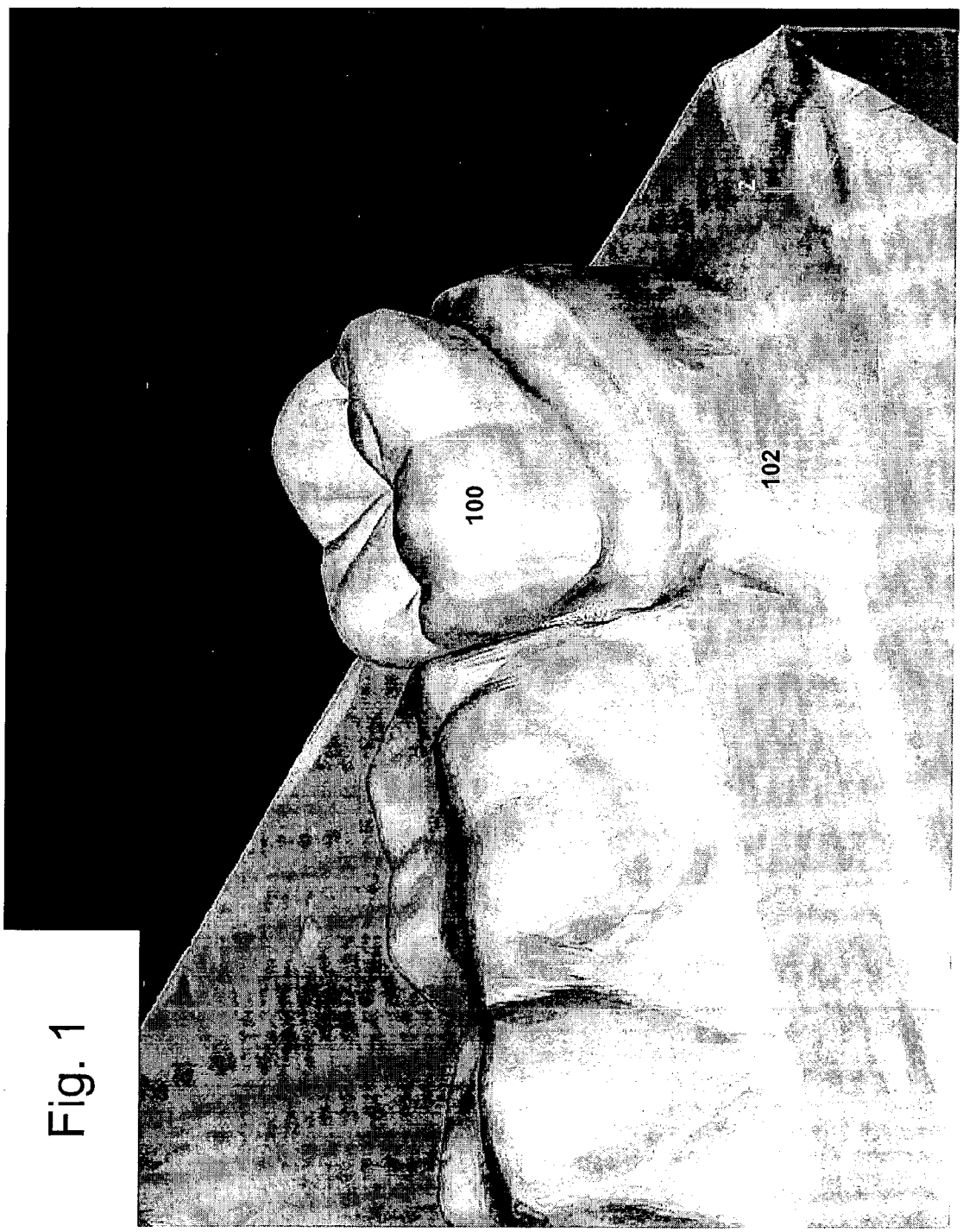
FIG. 1 illustrates an example of an electronic model for a dental crown constructed according to one embodiment of the present invention.

FIG. 1 illustrates an example of an electronic model for a dental crown constructed according to one embodiment of the present invention. In this example embodiment, a completed electronic model 100 for a crown is shown in the position it is to be installed within a patient's mouth as it is positioned within an electronic model for an impression of a patient's lower teeth. The electronic model for a patient's teeth corresponds to a polygonal mesh created from an electronic scan of a dental impression of a patient's mouth. An example of a system that generates such an electronic model is described within U.S. Provisional Patent Application entitled, "METHOD AND APPARATUS FOR COMPUTER GENERATION OF ELECTRONIC MODEL IMAGES", Ser. No. 60/351,270 filed Jan. 22, 2002, now U.S. patent application entitled, "METHOD AND APPARATUS FOR COMPUTER GENERATION OF ELECTRONIC MODEL IMAGES", Ser. No. 10/350,302, filed Jan. 22, 2003; and U.S. Provisional Patent Application entitled, "METHOD AND APPARATUS FOR AUTOMATICALLY DETERMINING THE LOCATION OF INDIVIDUAL TEETH WITHIN ELECTRONIC MODEL IMAGES", Ser. No. 60/351,271, filed Jan. 22, 2002, now U.S. patent application entitled, "METHOD AND APPARATUS FOR AUTOMATICALLY DETERMINING THE LOCATION OF INDIVIDUAL TEETH WITHIN ELECTRONIC MODEL IMAGES", Ser. No. 10/350,304, filed Jan. 22, 2003.

The output from the scanning process includes the generation of an electronic model representing the physical representation of the scanned study cost. The electronic model consisting of a polygonal mesh used to represent the seen face of the study cast. Such an electronic model may be created using a process described in commonly assigned U.S. Provisional Patent Application, "Method and Apparatus for Computer Generation of Electronic Model Images" Ser. No. 60/351,270, filed Jan. 27, 2002, now U.S. patent application, "Method and Apparatus for Computer Generation of Electronic Model Images" Ser. No. 10/305,302, filed Jan. 22, 2003.

Additionally, the electronic models may also be created using a CT Scan of an impression, rather than scanning the study cast, using commercially available CT scanning processes such as a process developed by Hytec Corp. of Los Alomos, N. Mex. This process also generates an electronic model consisting of a polygonal mesh. In both cases, the generated polygonal mesh is used in subsequent processing independent of the source of the electronic model.

An operator of a computing system generates an electronic model for the crown appliance as described herein to obtain a custom designed appliance that matches the available space in the patient's mouth. Once the electronic model for the crown appliance is completed to the satisfaction of the dental professional, the crown appliance may be manufactured using any manufacturing processing that accepts electronic models for physical objects expressed in a standard form. In a preferred embodiment, the manufacturing process utilizes a lost-wax manufacturing process in which the electronic model of the crown device is specified in a standard STL specification file. The STL specification file is used to generate a wax impression for the crown appliance using any type of rapid prototyping process that is well known in the prototyping industry. One skilled in the art will recognize that any type rapid prototyping processes may be used without deviating from the spirit and scope of the present invention as recited within the attached claims. In addition, throughout this application, an example embodiment is illustrated using the generation of a dental crown appliance; one skilled in the art will easily recognize that other CBI appliances may be readily constructed in accordance with the present invention as recited in the attached claims.

Figure 2:
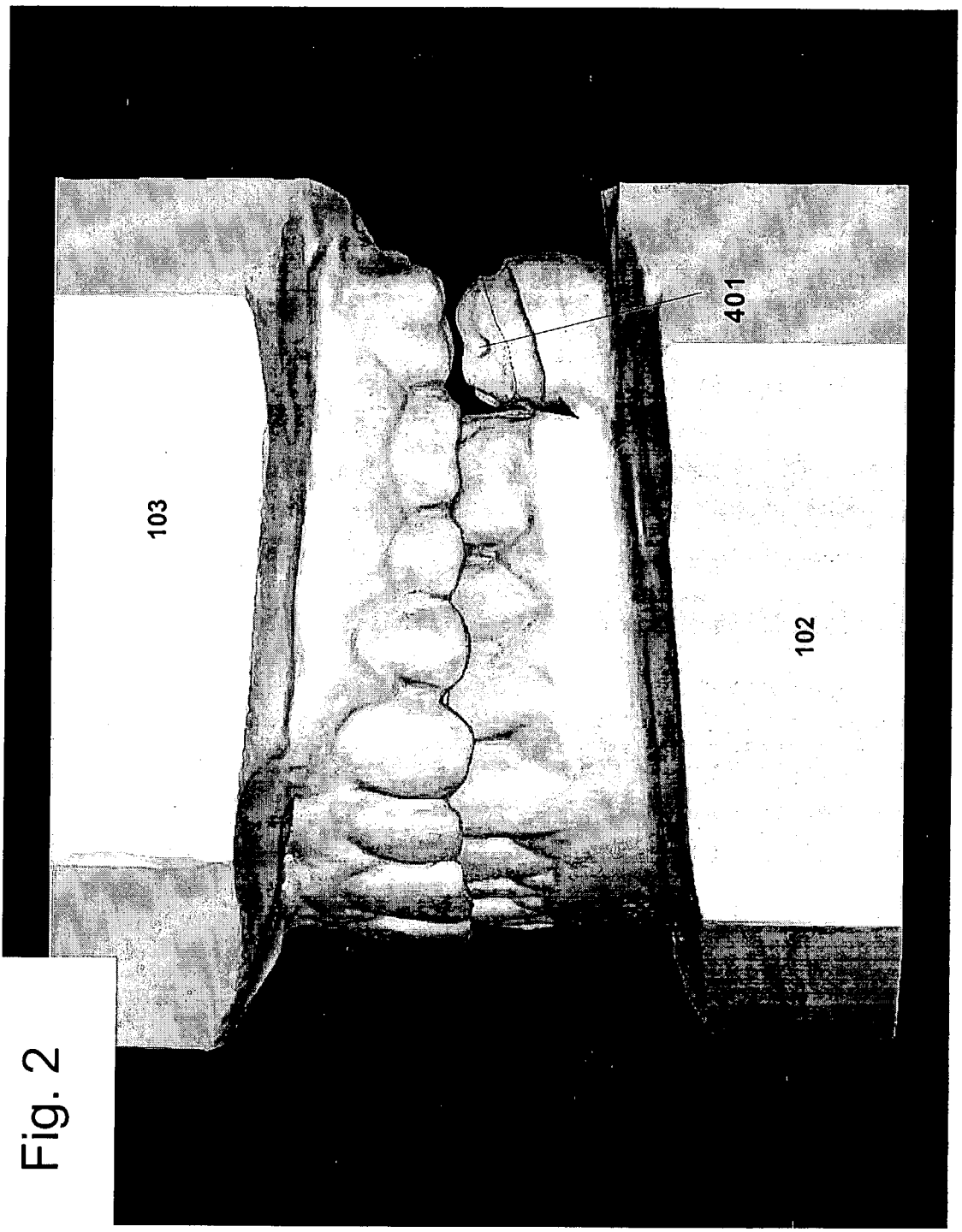
FIG. 2 illustrates a side view of an electronic model of a dental impression of a patient's teeth used in creation of a dental crown constructed according to one embodiment of the present invention.

FIG. 2 illustrates a side view of an electronic model of a dental impression of a patient's teeth used in creation of a dental crown constructed according to one embodiment of the present invention. In this embodiment, the dental impression model includes an upper teeth portion 103 and a lower teeth portion 102. The lower teeth portion 102 possesses a prep site 401 that represents the location at which a crown appliance is to be inserted. The upper teeth portion 103 are positioned relative to the lower teeth portion 102 to illustrate the interaction of the opposing teeth as a patient's mouth is opened and closed. In the position shown in FIG. 2, the teeth are positioned as they would be when the patient has his or her mouth completely closed. As disclosed in earlier applications of the assignee, the upper portion 103 and the lower portion 102 of the electronic model of these teeth may be moved relative to each other to permit the study of the interaction of opposing teeth, and in the instant application, opposing teeth and a crown appliance.

Figure 3:
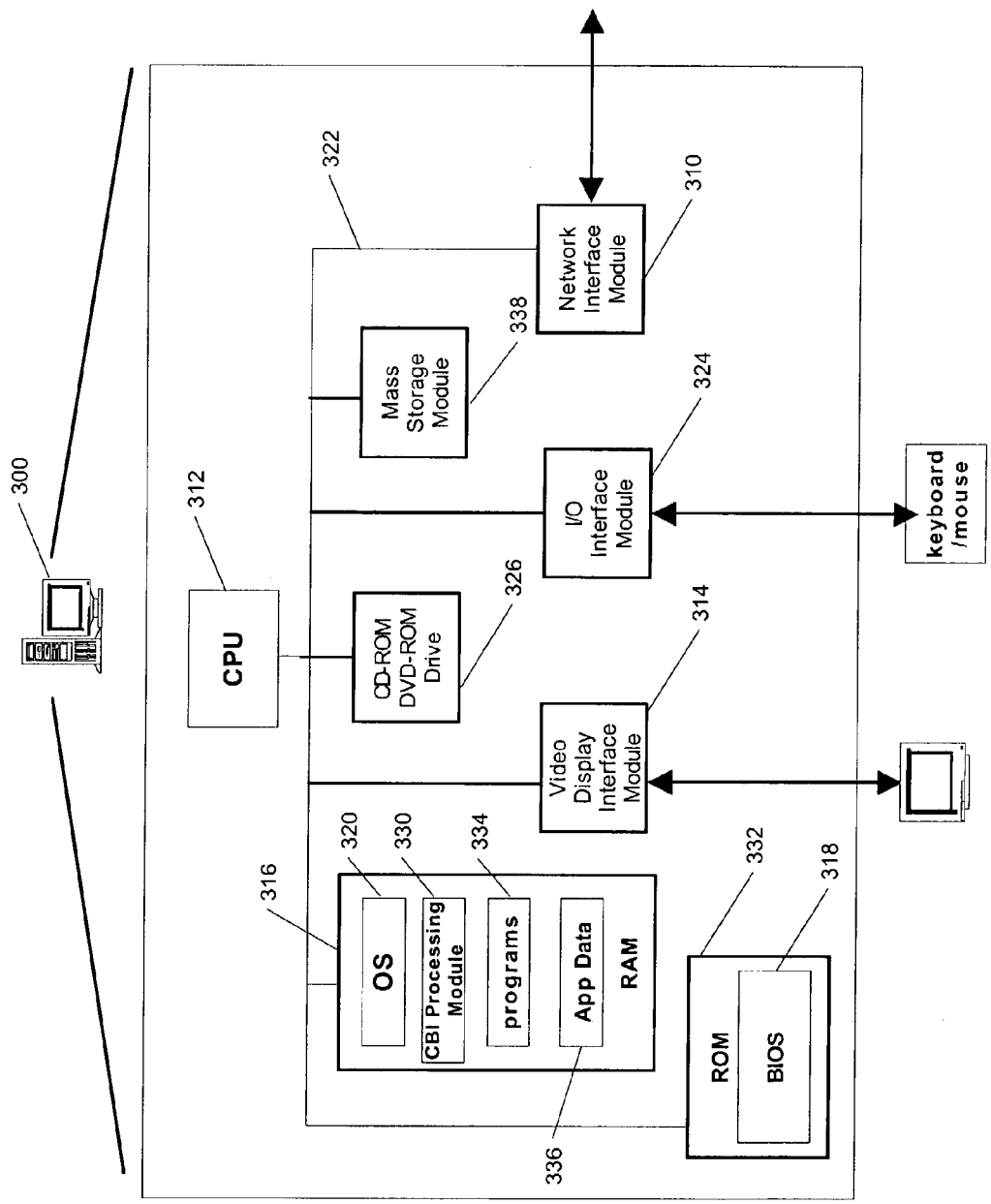
FIG. 3 illustrates a general purpose computing system for use in implementing as one or more computing embodiments of the present invention.

With reference to FIG. 3, an exemplary system for implementing the invention includes a general-purpose computing device in the form of a conventional personal computer 300, including a processor unit 312, a system memory 316, and a system bus 322 that couples various system components including the system memory 316 to the processor unit 312. The system bus 322 may be any of several types of bus structures including a memory bus or memory controller, a peripheral bus and a local bus using any of a variety of bus architectures. The system memory includes read only memory (ROM) 332 and random access memory (RAM) 316. A basic input/output system 318 (BIOS), which contains basic routines that help transfer information between elements within the personal computer 300, is stored in ROM 318.

The personal computer 300 further includes a hard disk drive 338 for reading from and writing to a hard disk, a magnetic disk drive for reading from or writing to a removable magnetic disk, and an optical disk drive 326 for reading from or writing to a removable optical disk such as a CD ROM, DVD, or other optical media. The hard disk drive 338, magnetic disk drive, and optical disk drive 326 are connected to the system bus 322 by a hard disk drive interface, a magnetic disk drive interface, and an optical drive interface, respectively. The drives and their associated computer-readable media provide nonvolatile storage of computer readable instructions, data structures, programs, and other data for the personal computer 300.

Although the exemplary environment described herein employs a hard disk 338, a removable magnetic disk, and a removable optical disk 326, other types of computer-readable media capable of storing data can be used in the exemplary system. Examples of these other types of computer-readable mediums that can be used in the exemplary operating environment include magnetic cassettes, flash memory cards, digital video disks, Bernoulli cartridges, random access memories (RAMs), and read only memories (ROMs).

A number of program modules may be stored on the hard disk 338, magnetic disk, optical disk 326, ROM 332 or RAM 316, including an operating system 320, one or more application programs 330, other program modules 334, and program data 336. A user may enter commands and information into the personal computer 300 through input devices such as a keyboard and mouse or other pointing device. Examples of other input devices may include a microphone, joystick, game pad, satellite dish, and scanner. These and other input devices are often connected to the processing unit 312 through a I/O port interface 324 that is coupled to the system bus 332. Nevertheless, these input devices also may be connected by other interfaces, such as a parallel port, game port, or a universal serial bus (USB). A monitor or other type of display device is also connected to the system bus 332 via an interface, such as a video adapter 314. In addition to the monitor, personal computers typically include other peripheral output devices (not shown), such as speakers and printers.

The personal computer 300 may operate in a networked environment using logical connections to one or more remote computers, such as a remote computer. The remote computer may be another personal computer, a server, a router, a network PC, a peer device or other common network node, and typically includes many or all of the elements described above relative to the personal computer 300. The network connections include a local area network (LAN) and a wide area network (WAN). Such networking environments are commonplace in offices, enterprise-wide computer networks, intranets, and the Internet.

When used in a LAN networking environment, the personal computer 300 is connected to the local network through a network interface or adapter 310. When used in a WAN networking environment, the personal computer 300 typically includes a modem or other means for establishing communications over the wide area network, such as the Internet. The modem 254, which may be internal or external, is connected to the system bus 332 via the I/O port interface 324. In a networked environment, program modules depicted relative to the personal computer 300, or portions thereof, may be stored in the remote memory storage device. It will be appreciated that the network connections shown are exemplary, and other means of establishing a communications link between the computers may be used.

Additionally, the embodiments described herein are implemented as logical operations performed by a computer. The logical operations of these various embodiments of the present invention are implemented (1) as a sequence of computer implemented steps or program modules running on a computing system and/or (2) as interconnected machine modules or hardware logic within the computing system. The implementation is a matter of choice dependent on the performance requirements of the computing system implementing the invention. Accordingly, the logical operations making up the embodiments of the invention described herein can be variously referred to as operations, steps, or modules.

Figure 4A:
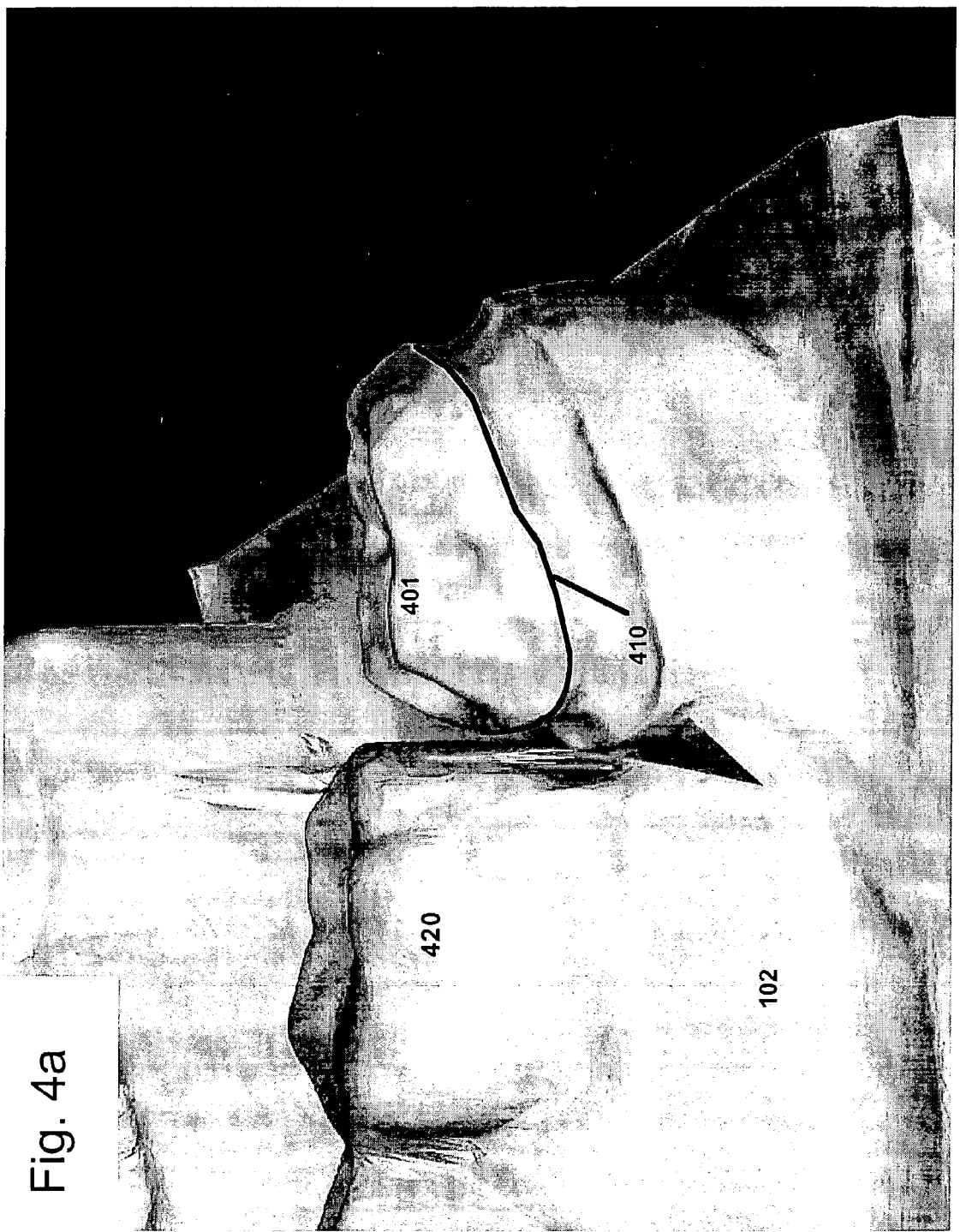
FIGS. 4a–4c illustrate various views of a tooth prep site used to construct a dental crown according to one embodiment of the present invention.
Figure 4B:
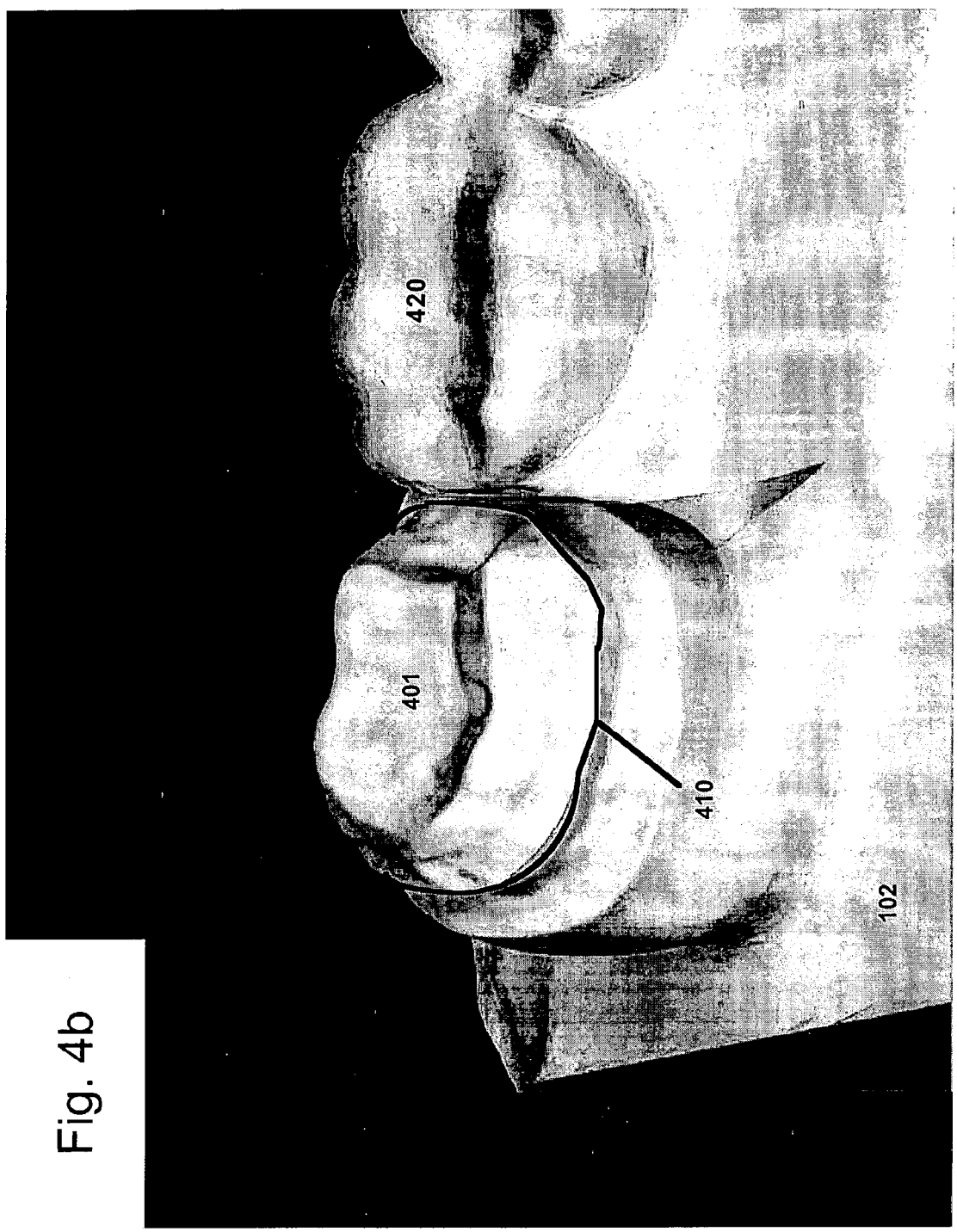
Figure 4C:
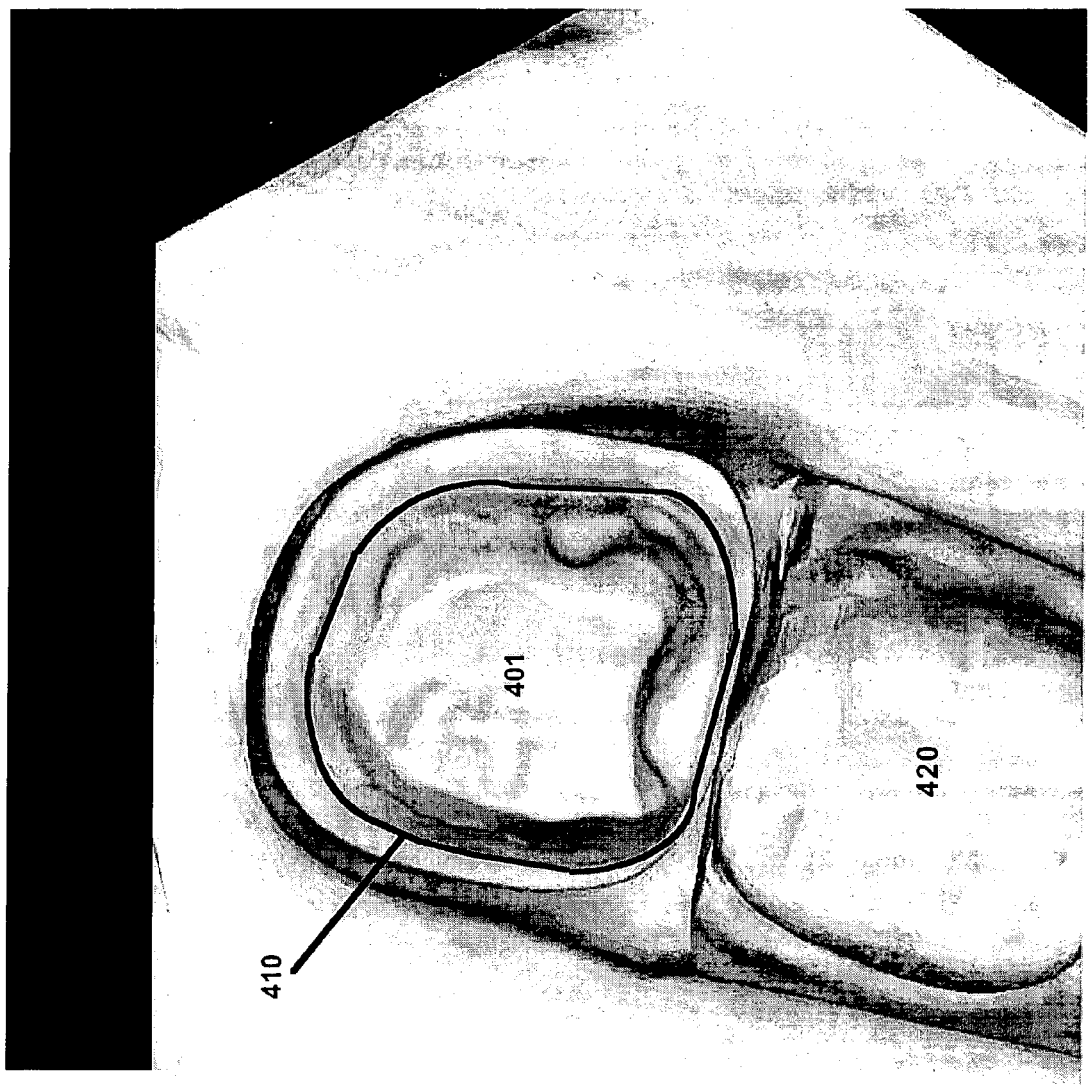

FIGS. 4a–4c illustrate various views of a tooth prep site used to construct a dental crown according to one embodiment of the present invention. In these figures, a prep site 401 that represents a location on an electronic model where a crown appliance it to be constructed and installed. The prep site 401 is typically defined as the portion of the patient's tooth that is to be covered by a crown appliance. The area underneath the crown appliance is defined to be the area within a margin curve 410 that identifies the point in space where the patient's existing tooth meets the outer edge of the crown appliance. When the crown appliance is installed within the patient's mouth, the margin curve will define the transition from the patient's teeth and jaw structure to an outer surface of the crown. FIG. 4a illustrates the prep site 401 and the margin curve 410 as it would be seen from the outer side of teeth. FIG. 4b illustrates the same prep site 401 and the corresponding margin curve 410 as it would be seen from the inner side of teeth. FIG. 4c illustrates the prep site 401 and its margin curve 410 as it would be seen from top view of the teeth. The margin curve 410 is shown in FIG. 4c as completely encircling the prep site 401 as the crown appliance will cover the entire prep site 401.

Figure 5:
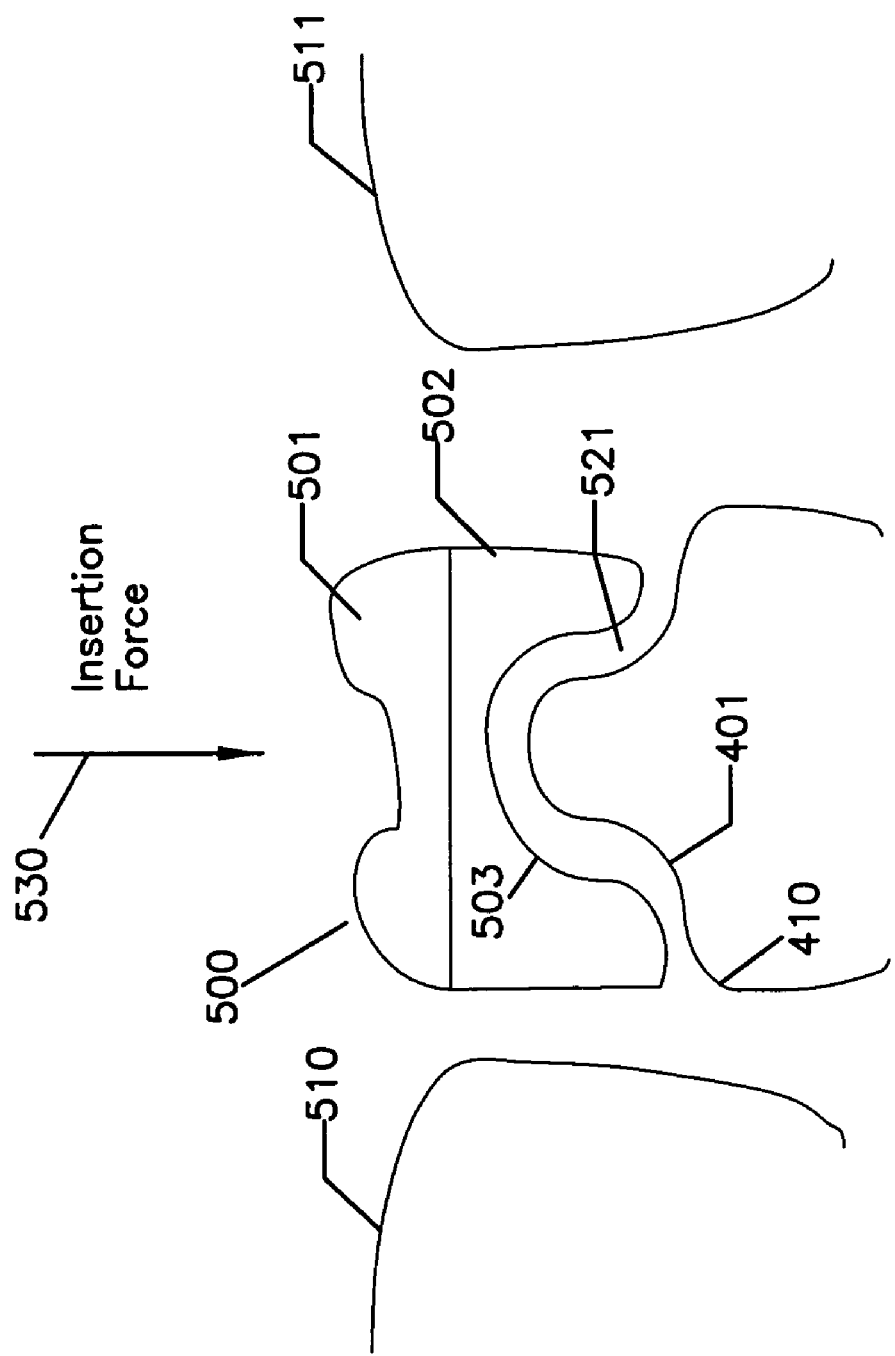
FIG. 5 illustrates a cross-section view of a crown, its corresponding prep site and adjacent teeth in preparation for construction of a dental crown in accordance with an embodiment of the present invention.

FIG. 5 illustrates a cross-section view of a crown, its corresponding prep site and adjacent teeth in preparation for construction of a dental crown in accordance with an embodiment of the present invention. In this embodiment, a crown appliance 500 constructed from a crown top 501, a crown side 502, and a crown offset prep 503 polygonal mesh is placed upon a prep site 401. The crown appliance 500 is shown relative to its adjacent teeth 510, 511. The crown top 501 corresponds to the top portion of a crown that corresponds to the occlusal surface that interacts with an opposing tooth. Typically, the crown top 501 is selected from a library of crown shapes that are stored within a computer-based dental modeling system. This library of teeth are pre-constructed shapes that represent the various teeth known to be within a human mouth. The dental professional selects the crown top 501 from the library that corresponds to the type of tooth to be created by the crown appliance.

In a preferred embodiment, this library of crown tops comprise electronic polygonal mesh representation of standard crown shapes that have been scanned using a process similar to the one used to generate the electronic model of the patient's teeth 102, 103. For example, the University of Minnesota School of Dentistry is known to possess a standard set of crown top shapes that have been modeled by Professor Fred Nobel to provide representative tooth shapes. These shapes have been sculpted to both provide useful opposing tooth surfaces needed by a patient in chewing food and provide aesthetically pleasing teeth in a patient's mouth. Of course, any such library of crown top shapes may be utilized with the present invention without deviating from the spirit and scope of the present invention as recited within the attached claims. Alternatively, electronic models of crown tops, such as ones commercially available from Productivity Training Corporation, of Morgan Hill Calif., may also be used without deviating from the spirit and scope of the present invention as recited in the attached claims.

The crown side 502 corresponds to the polygonal mesh created to mate the crown top 501 to the margin curve 410 along the outer edge of the crown appliance 500. Once a crown top 501 is selected, sized properly, and placed into its proper position, the crown side 502 may be constructed to define this outer shape of the crown appliance 500. The shape of the crown side 502 may be checked for its position relative to the adjacent teeth 510, 511 for regions of space where the surfaces may co-exist. The shape of the crown side 502 may be modified as needed to create adequate separation from the crown appliance 500 and the adjacent teeth 510, 511.

The crown offset prep 503 polygonal mesh corresponds to the inner surface of the crown appliance 500 and is shaped to correspond to the contours of the prep site 401 within the margin curve 410. The crown offset prep 503 mesh is defined to provide an offset space 521 between the prep site 401 and the crown offset prep 503 mesh that is sufficient to permit an adhesive to be placed between the prep site surface 401 and the crown appliance 500 that will hold the crown appliance 500 in place. The area between the crown top 501, crown side 502, and the crown offset prep 503 mesh represents the region of space to be filled by the crown appliance material, such as gold or ceramic dental material.

The crown prep mesh 503 is also checked to ensure that the crown appliance may be placed onto the prep site 401 along a path of an insertion vector 530. The completed crown appliance is typically installed following a straight vector path of travel. As a result, the inner shape of the offset prep mesh 503 is checked to identify and eliminate any undercut shapes in its surface that would prevent the insertion of the crown appliance onto the prep site. Typically, additional space is left in the offset space 521 for this undercut volume that may be filled by additional adhesive.

The processing system generates an electronic specification for the combination of these three polygonal meshes, the crown top 501, crown side 502, and the crown offset prep 503 meshes. This electronic specification is used to generate the rapid prototyping wax that may be used in a conventional lost wax manufacturing technique to create the crown appliance 500.

Figure 6A:
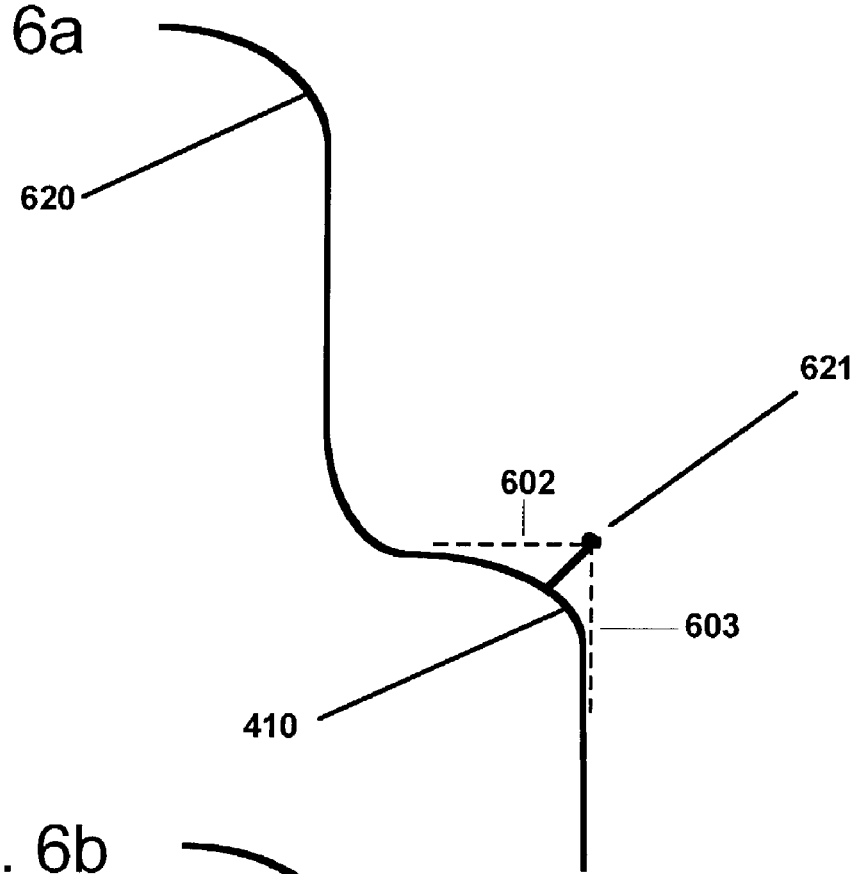
FIGS. 6a–6b illustrate creation of a refined margin curve point used in construction of a dental crown in accordance with another embodiment of the present invention.
Figure 6B:
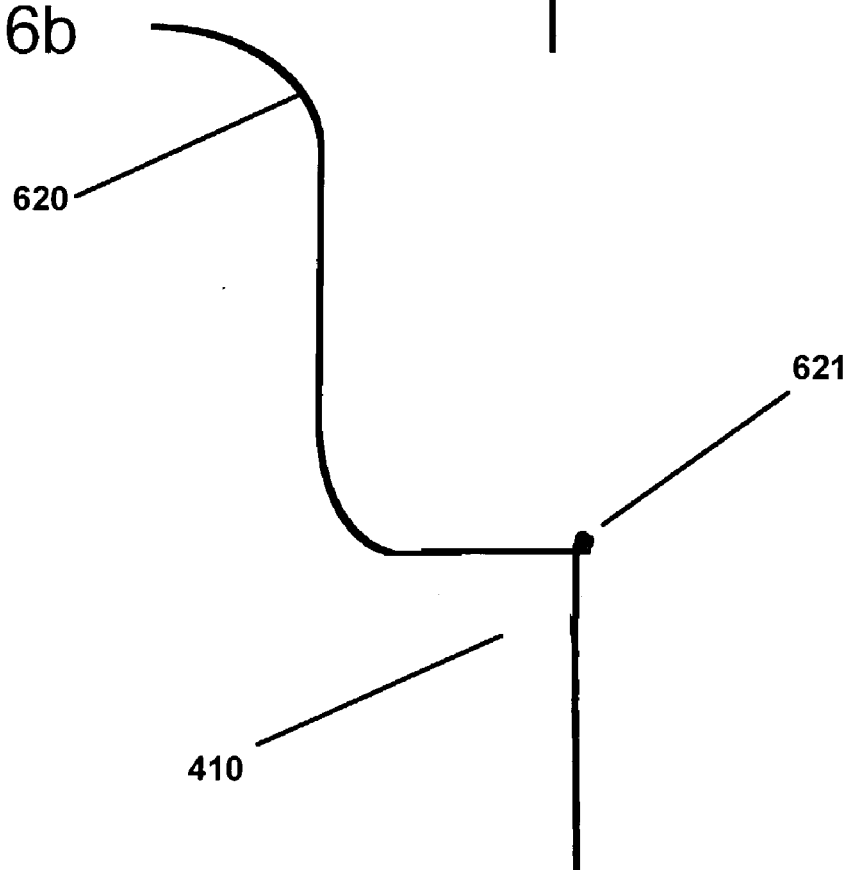

FIGS. 6a–6b illustrate creation of a refined margin curve point used in construction of a dental crown in accordance with another embodiment of the present invention. In a preferred embodiment, the margin curve 410 that is used to define the transition point between a patient's teeth and the crown appliance 100 is moved to a refined curve point 621 within the electronic model of the teeth 102. Typically, the margin curve point 410 appears as having a rounded edge as shown in FIG. 6a. This rounded edge appears to be created from the scanning and processing within the electronic modeling system 300 and may not accurately represent the point in space where the margin curve should exist.

As a result, the refined margin curve 621 is defined by projecting a line tangent to the horizontal 602 and vertical 603 surfaces from the prep site 401 on either side of the margin curve 410. The point of intersection for these two projected tangent lines 602, 603 is defined as the refined margin curve point for any given point on the margin curve. The prep site 401 surface of the polygonal mesh is modified to move the margin curve point 410, and its corresponding adjacent surface to the refined margin curve point 621 as shown in FIG. 6b. This process is shown for a single point on the margin curve surface 410 and is repeated for all points along the margin curve surface 410. The revised margin curve 621 is used in all subsequent processing to generate the crown appliance 500.

Figure 7B:
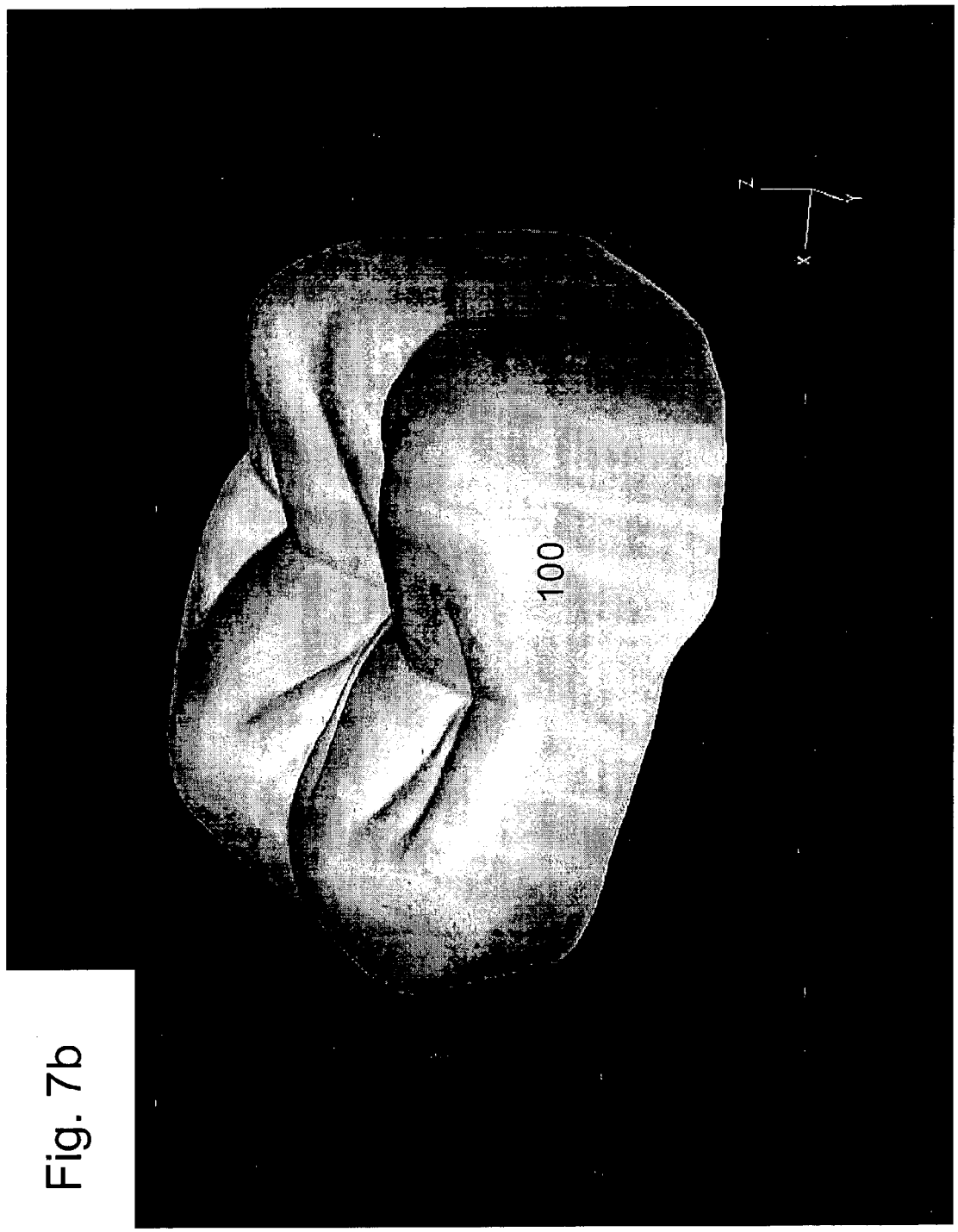
Figure 7C:
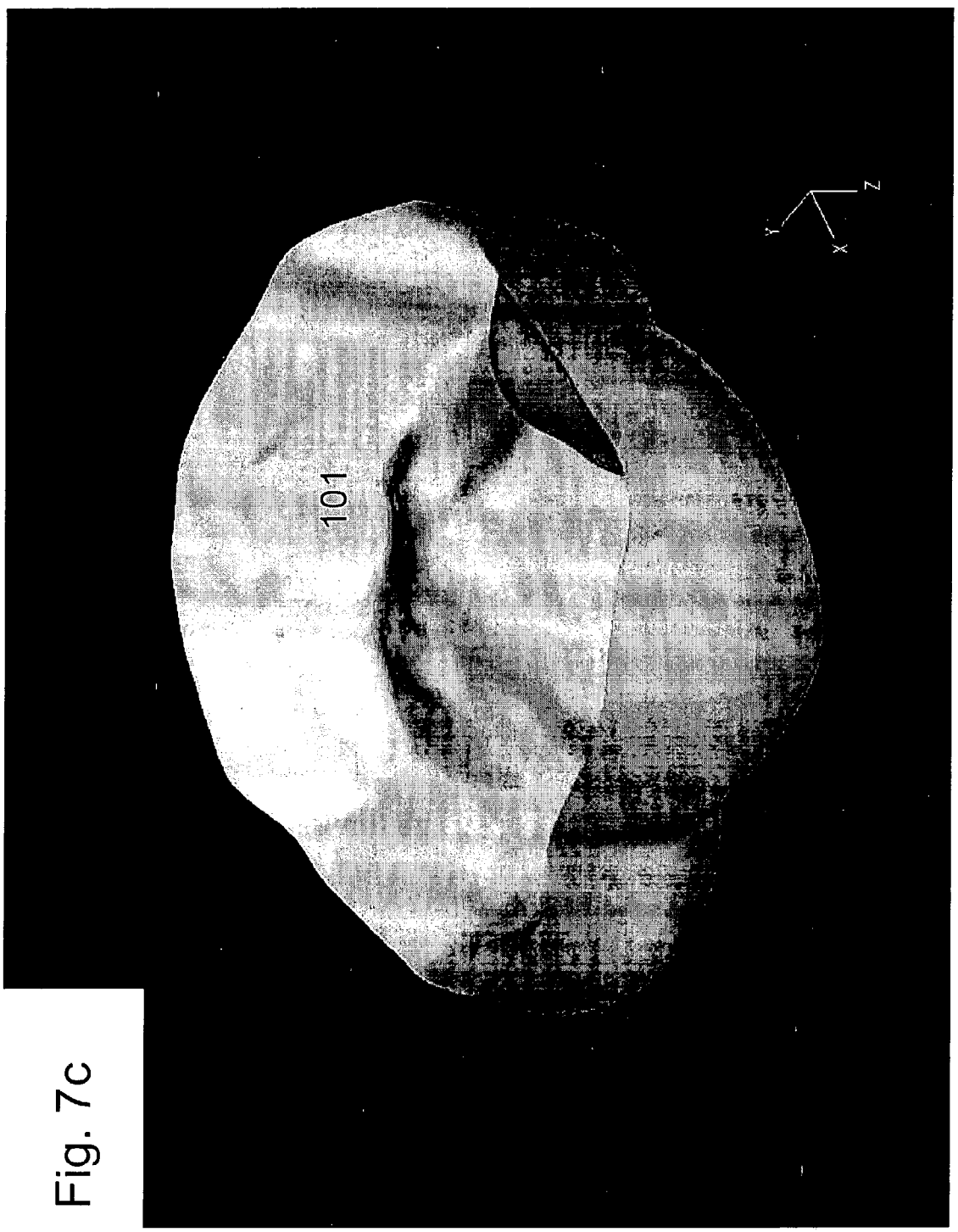
Figure 7D:
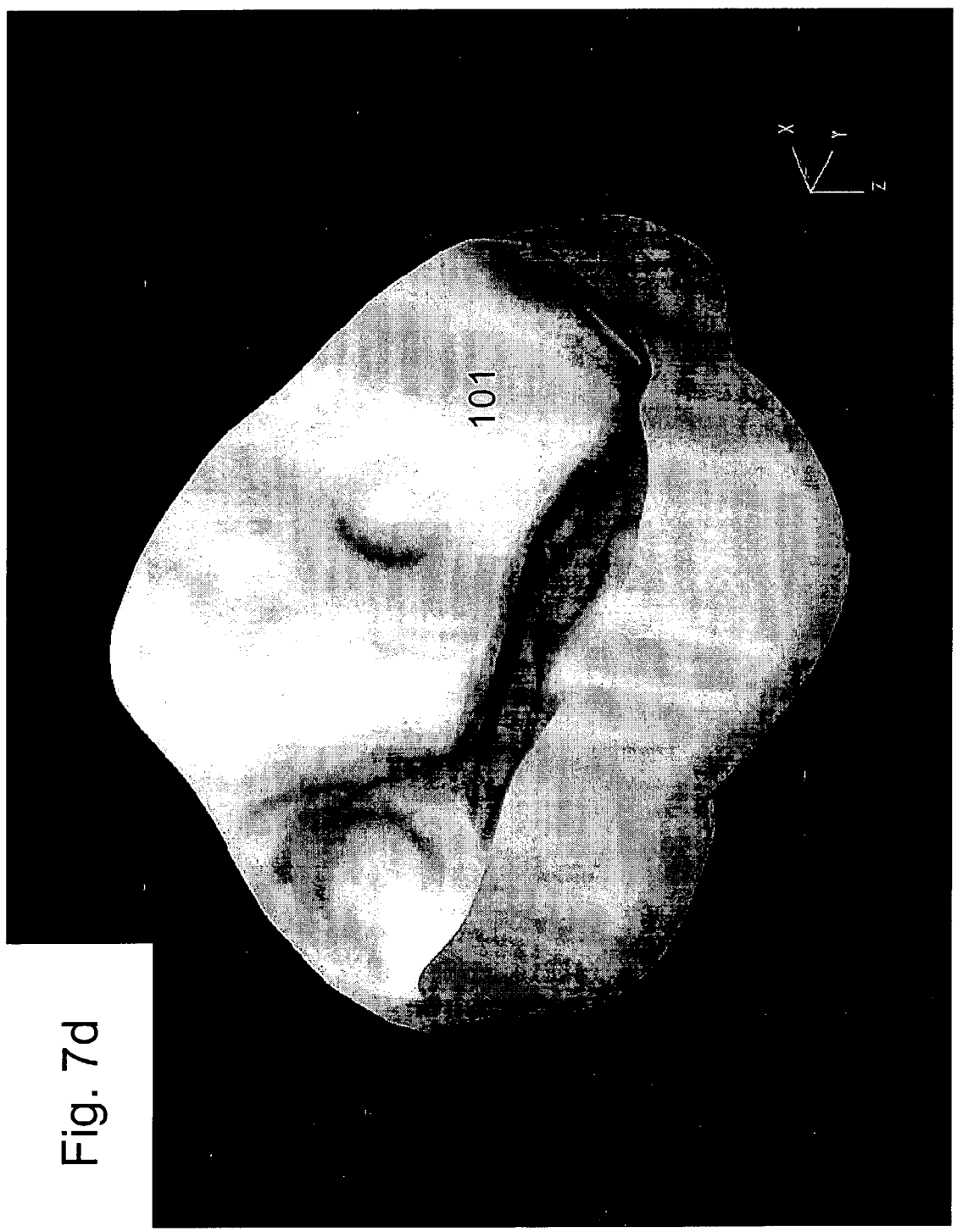

FIGS. 7a–7d illustrate various views of an electronic model for a dental crown constructed according to an embodiment of the present invention. FIGS. 7a and 7b illustrate the crown appliance 100 shown from the crown top perspective. FIGS. 7c and 7d illustrate the crown appliance 101 from the crown offset prep mesh perspective. When one compares the surface of the offset prep mesh shown in FIGS. 7c and 7d, the surfaces match the prep site surfaces shown in detail in FIGS. 4a–4c. The shape of the bottom edge of the crown appliance 100 also matches the margin curve 410 discussed above with respect to FIGS. 4a–4c.

Figure 8:
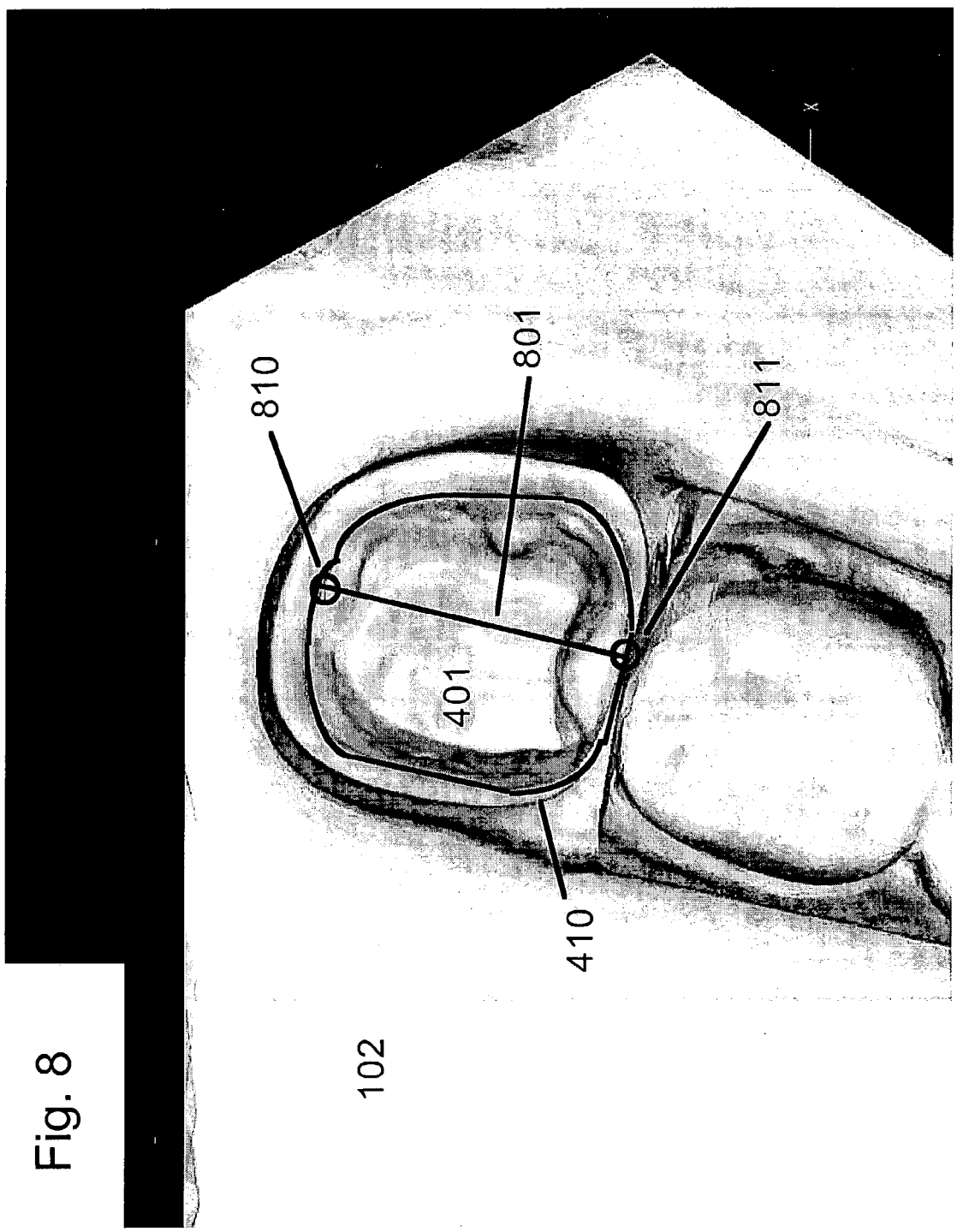
FIG. 8 illustrates identification of match points on an electronic model of dental impressions of teeth used to size a crown device according to an example embodiment of the present invention.

FIG. 8 illustrates identification of match points on an electronic model of dental impressions of teeth used to size a crown device according to an example embodiment of the present invention. In order to create the crown appliance 100 shown above in FIGS. 7a–7d, a crown top is selected from the library of electronic models for the crown tops. These library models are sized to a normalized size and are adjusted to fit the individual patient. The crown top is sized to fit the prep site 401 by an operator selecting at least two points 810–811 along a line 801 across one dimension of the prep site 410. Typically, the line 801 is selected such that end points 810–811 correspond to the widestpoints across the particular dimension of the prep site 401. These points also lie on the margin curve 410.

Once these two points are selected, the length of the line 801 is determined for use in properly sizing the crown top. The normalized crown top is scaled in size to correspond to the length of the identified line 801. The crown top is scaled in all dimensions to preserve the relationships and aspect ration for the crown top. If more than two points are selected, the crown top may be scaled in additional dimensions to fit the prep site 401. Typically, only one line is selected as it permits the crown top to scale in a manner that preserves the occlusal shape of the crown top.

Figure 9A:
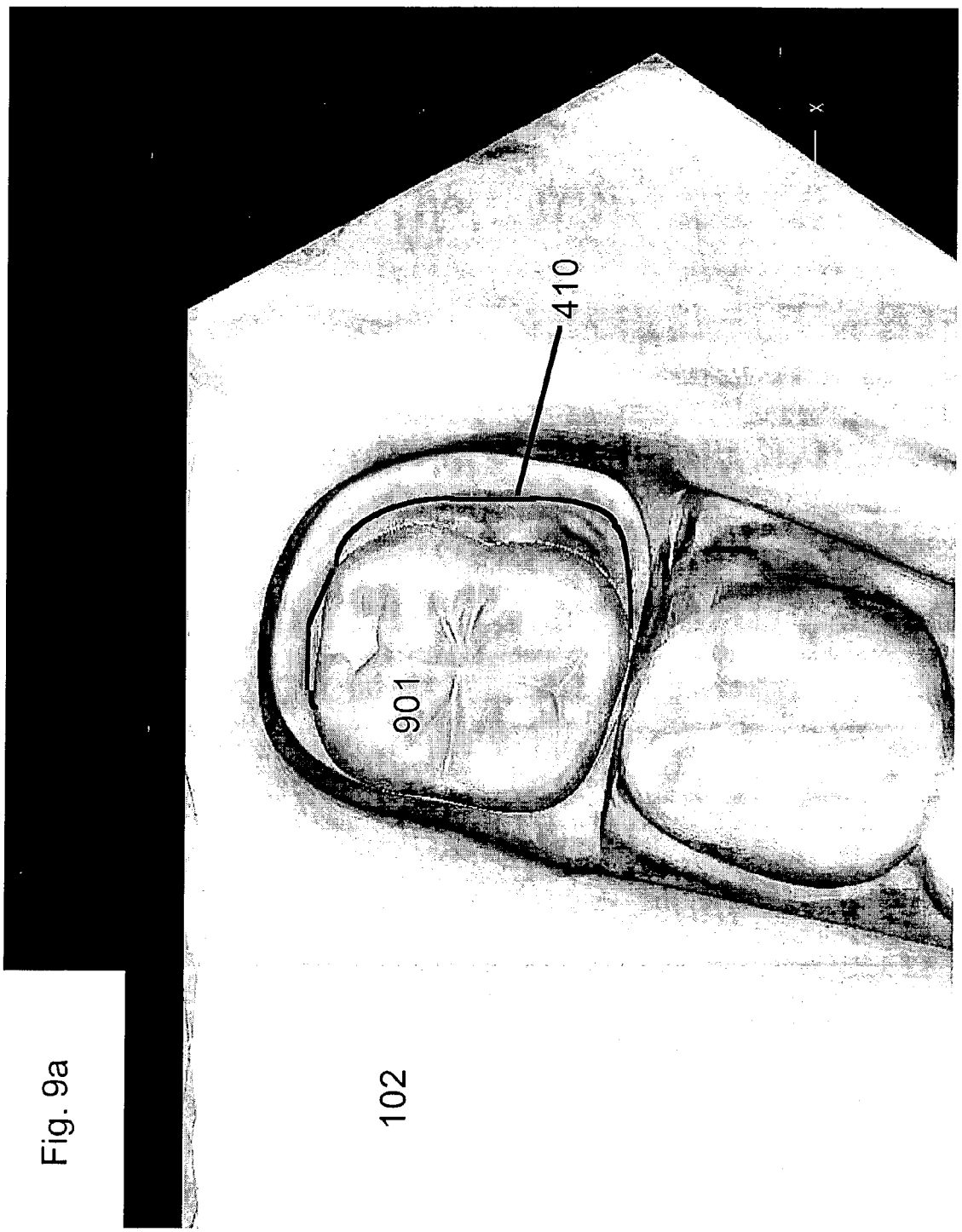
FIGS. 9a–9b illustrate placement of a dental crown upon a prep site using previously selected match points according to an embodiment of the present invention.
Figure 9B:
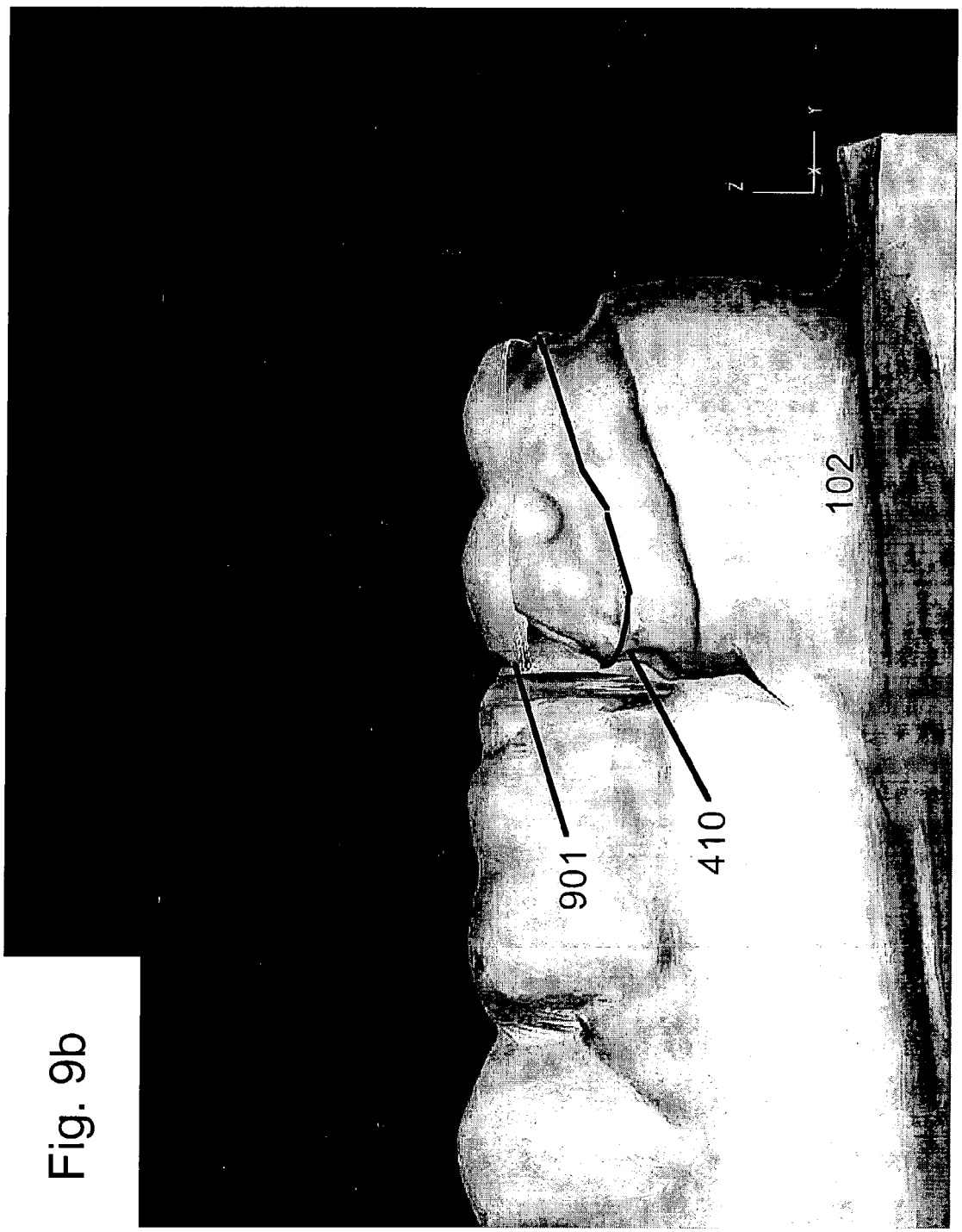

FIGS. 9a–9b illustrate placement of a dental crown upon a prep site using previously selected match points according to an embodiment of the present invention. The scaled crown top 901 is placed upon the prep site in the position in which it is expected to reside once installed. The computing system superimposes the electronic model of the crown top 901 upon the electronic model of the jaw 102 containing the prep site 401. The placement of the crown top 901 may be viewed from a top view as shown in FIG. 9a and a side view as shown in FIG. 9b. The margin curve 410 is shown in these views to identify the prep site and allow proper placement of the crown top 901.

The operator may move and position the crown top 901 into position that corresponds to a desired location once the crown appliance is completed. This manual process of placing and orienting the crown top continues until the position satisfies the dental professional.

Figure 10B:
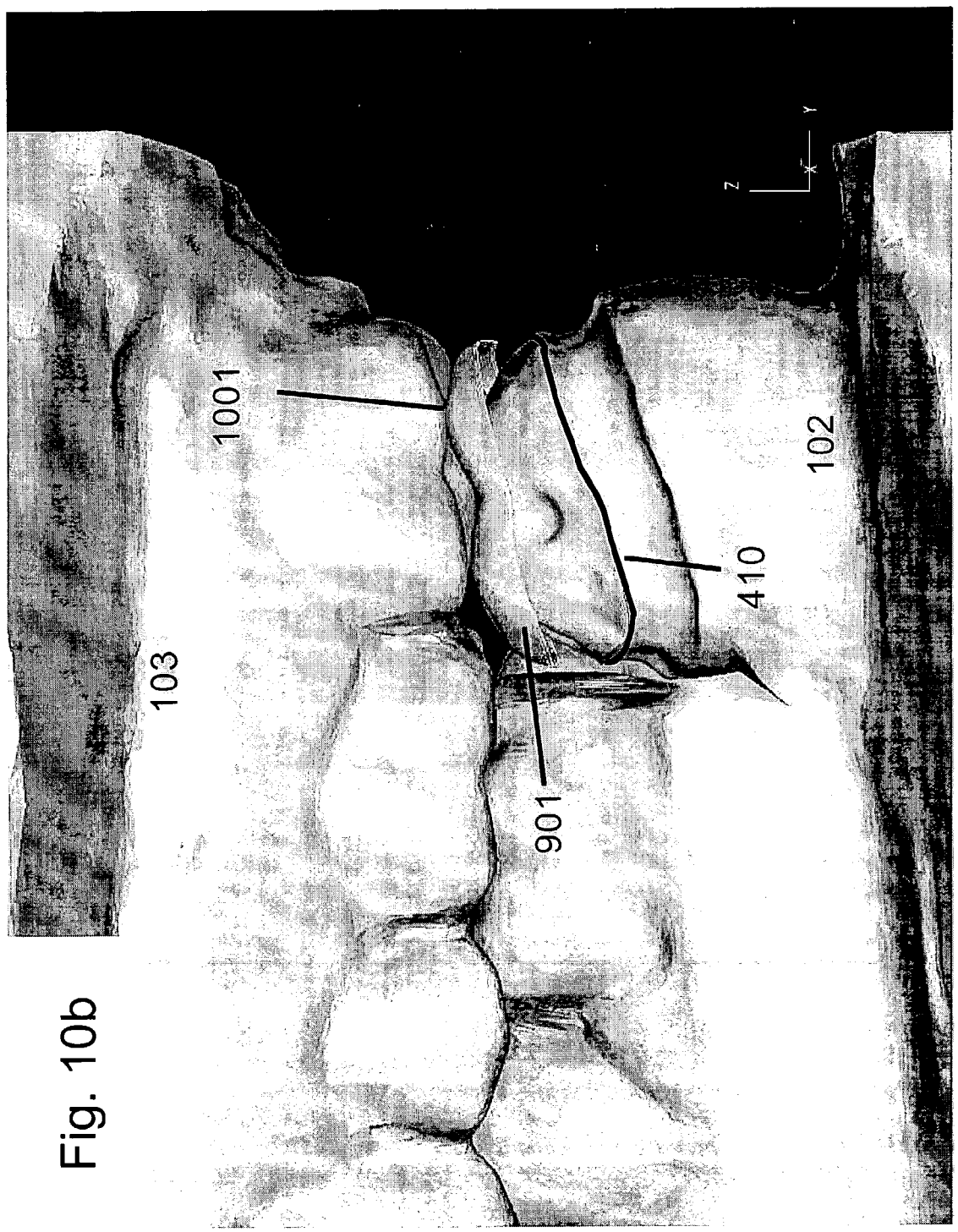

FIGS. 10a–10c illustrate correcting placement and orientation of a dental crown upon a prep site using previously selected match points according to an embodiment of the present invention. The crown top 901 must also be oriented to place the top surface of the crown top in a position to properly engage the opposing tooth. FIG. 10a illustrates the shifting of the orientation of the crown top 901 to a desired position that appears to more accurately track the orientation of the margin curve. FIG. 10b illustrates positioning the upper teeth model 103 into their position to verify that the crown top 901 properly interacts with the opposing tooth. The operator may again modify the position and orientation of the crown appliance 901 to allow points of contact 1001 between the crown top 901 and the opposing teeth 103 to be properly positioned as is FIG. 10c.

Because the computing system permits the electronic models to be rotated and moved in any direction, the operator may verify the position and interaction 1002 of the crown top 901 with the other teeth of the patient until satisfied that the crown top 901 is position in the optimum position. Once positioned, the computing system may define the side mesh and the offset prep mesh between the crown top and the margin curve 410 as discussed above.

Figure 11A:
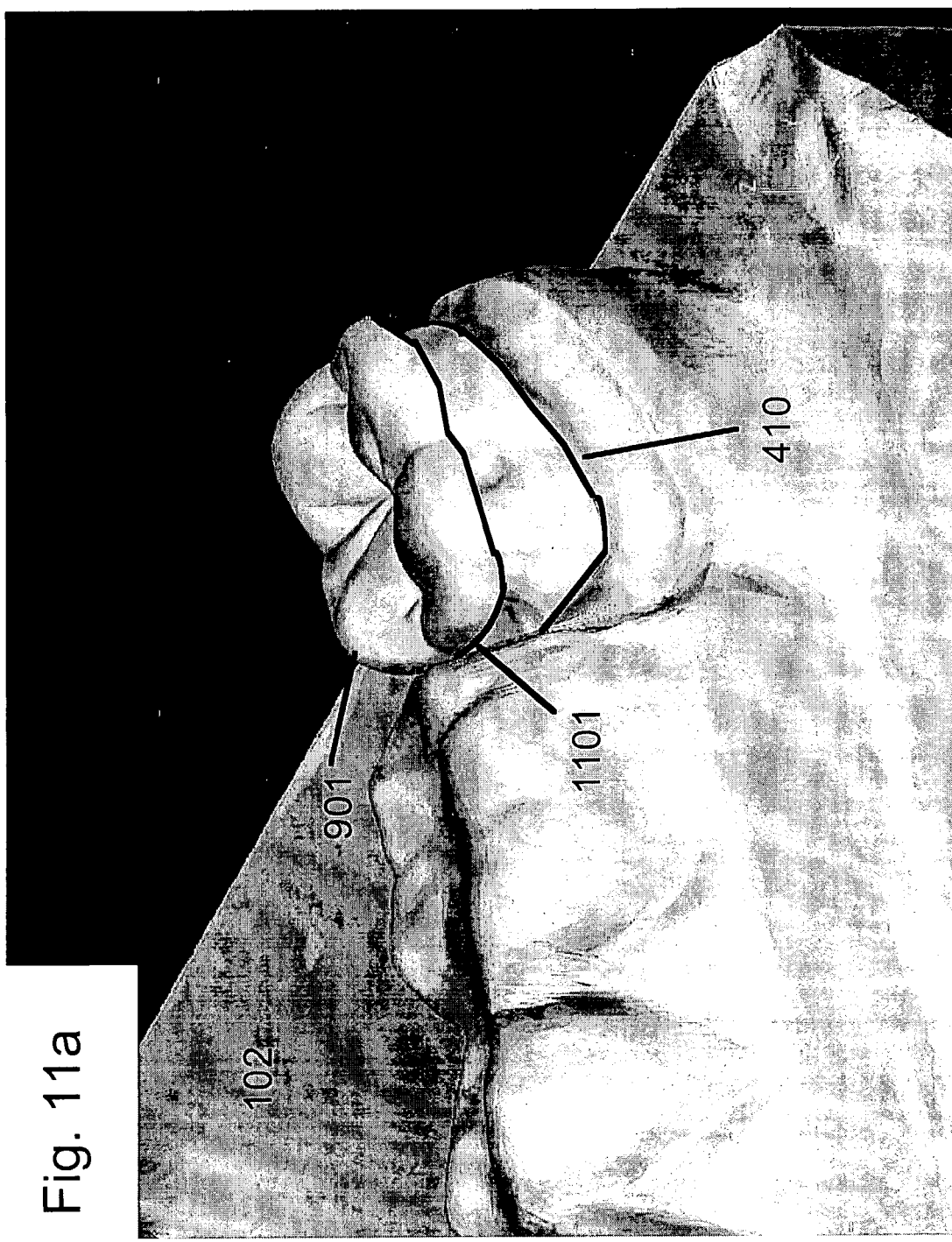
FIGS. 11a–11b illustrates electronic construction of side meshes between a properly oriented crown and a margin curve of a prep site according to an embodiment of the present invention.
Figure 11B:
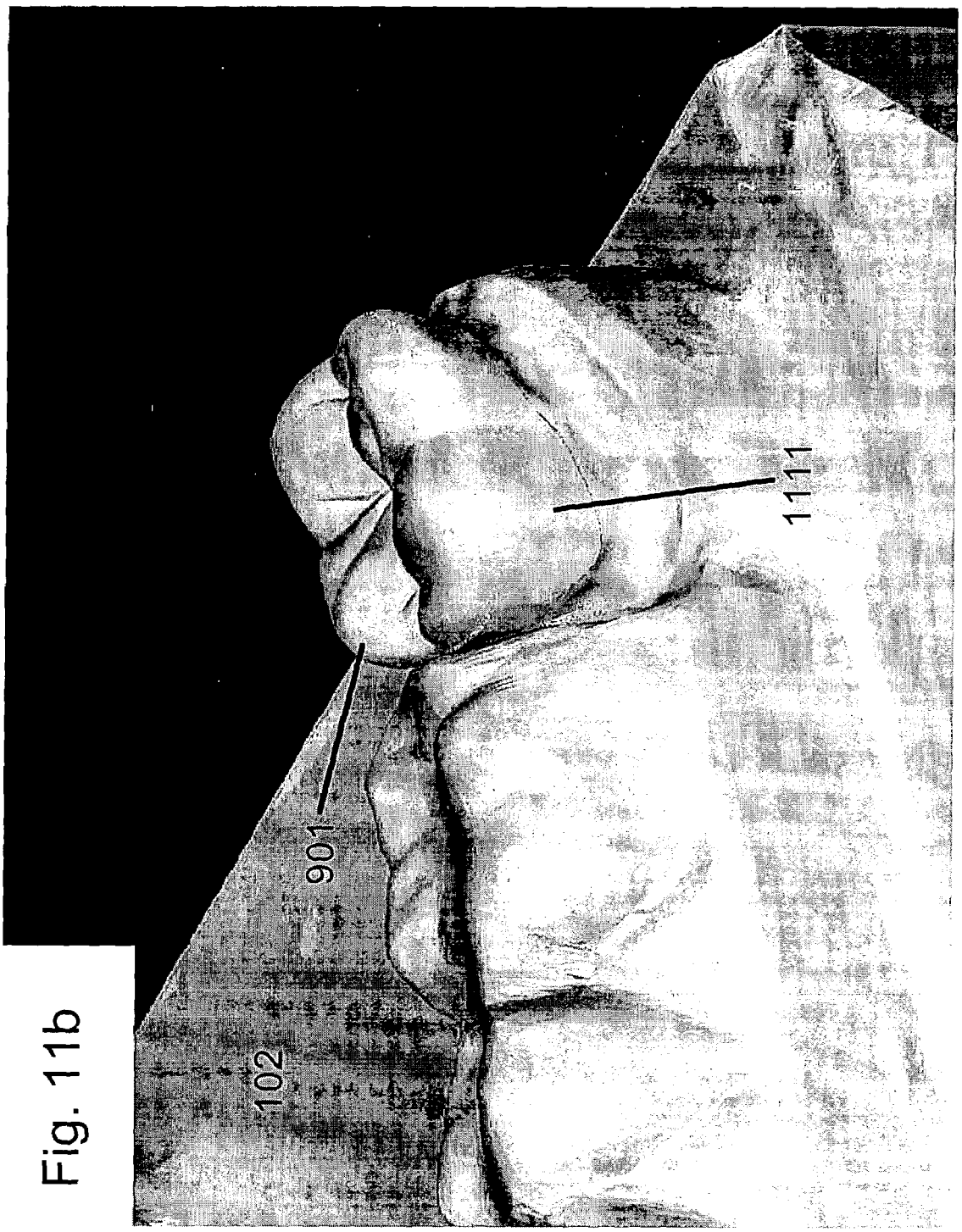

FIGS. 11*a*–11*b* illustrates electronic construction of side meshes between a properly oriented crown and a margin curve of a prep site according to an embodiment of the present invention. The side mesh is constructed to create a smooth surface between the edge 1101 of the crown top 901 and the margin curve 410. Any smooth shape, that typically possesses a modest curve, may be used to create a crown appliance that is both functional and aesthetically pleasing. The operator defines these two curves 1101 and 410 and the computer system automatically generates a side mesh as shown in FIG. 11*b*. The side mesh is also created to avoid interaction with the adjacent teeth. The operator modifies the side mesh as necessary to obtain the desired shape.

The offset prep mesh is also automatically created to provide at least a minimum offset space between the offset prep mesh and the prep site 401. The three meshes, the crown top mesh, the side mesh and the offset prep mesh are combined together to define the final volume for the crown appliance.

Figure 12A:
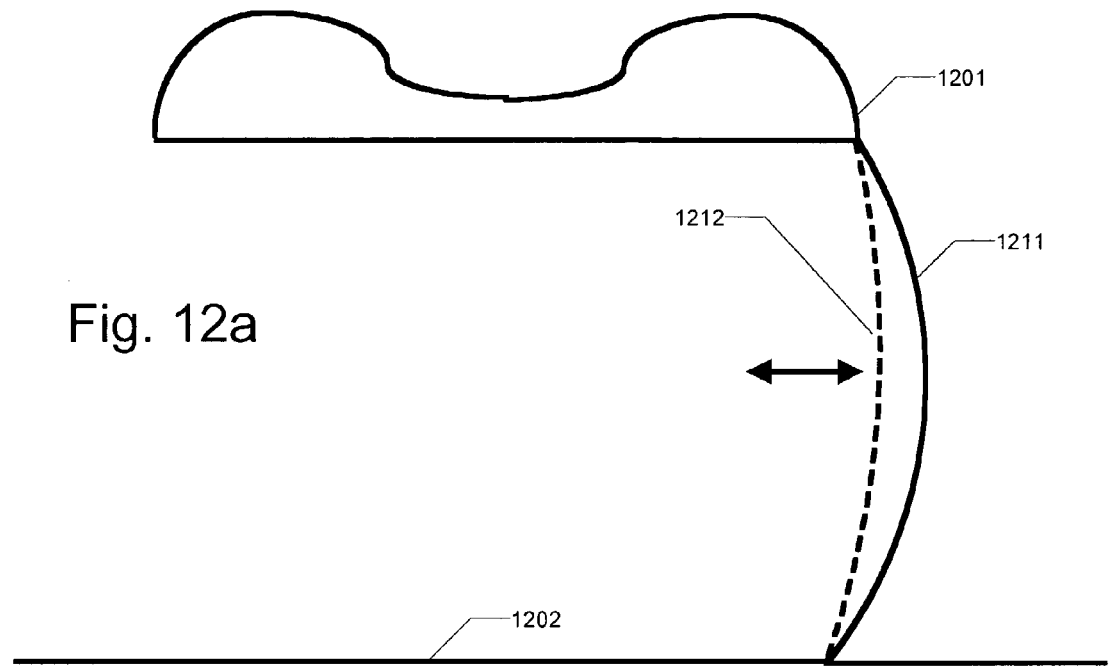
FIGS. 12a–12b illustrate electronic construction of side meshes having various curved shapes between a properly oriented crown and a margin curve of a prep site according to an embodiment of the present invention.
Figure 12B:
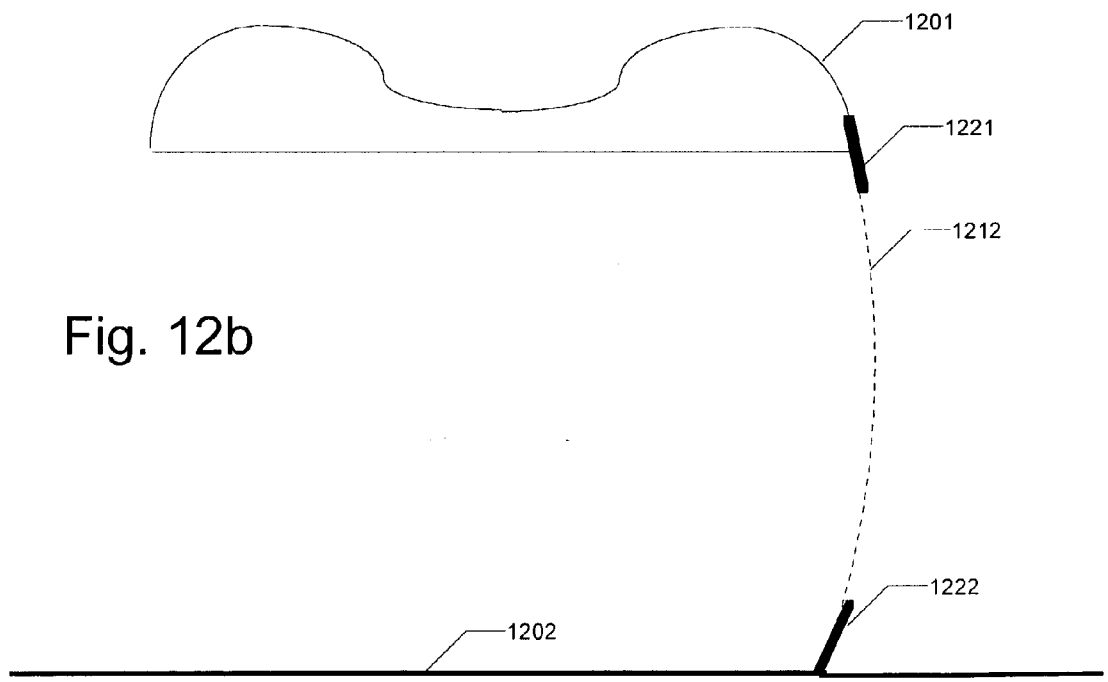

FIGS. 12*a*–12*b* illustrate electronic construction of side meshes having various curved shapes between a properly oriented crown and a margin curve of a prep site according to an embodiment of the present invention. FIG. 12*a* illustrates the shape of the side mesh being varied to obtain a desired shape and avoid the interaction of the side of the crown appliance with adjacent teeth. In this example, a crown top 1201 is shown above a margin curve 1202. A side mesh 1211 is shown connecting the two surfaces. The operator may modify the shape of the side mesh by moving the surface 1212 to a desired position. Any type of graphical manipulation of the side surface may be used as part of the shaping of the sides of the crown.

In a preferred embodiment, a user specifies one or more parameters that are used to specify the rate of change for the slope of the side surface. The side surface 1212 is defined by a plane tangent 1221 to the crown top 1201 at the point where the two surfaces interface. Similarly, the side surface is defined by a plane tangent 1222 at the margin line 1202. The side surface 1212 is defined as a series of polygonal surfaces along a path between these two planes where the slope of the surface is varied from the slope of the first tangent plane 1221 and the second tangent plane 1222. The side surfaces are typically varied to allow the side surface to contact adjacent teeth to prevent movement of the tooth while still providing sufficient spacing to permit the insertion of the crown onto the prep site. The user may vary the parameters to obtain a desired shape for the side surfaces. The process will continue until the dental professional is satisfied with the shape of the side mesh.

Once the electronic model for the crown appliance is completed, the crown appliance may be manufactured using any manufacturing processing that accepts electronic models for physical objects expressed in a standard form as discussed above. In a preferred embodiment, a standard STL specification file is utilized to define the volume for the crown appliance that is to be manufactured. The STL specification file is used generate a wax impression for the crown appliance using a rapid prototyping process that is well known in the prototyping industry. The wax impression may be used in a lost-wax fabrication process to make the crown appliance out of any suitable dental material such as gold or ceramic material. Of course, one skilled in the art will recognize that any type of rapid prototyping methods may be utilized to make such CBI products without deviating from the spirit and scope of the present invention as recited within the attached claims. One such alternative rapid prototyping process is a deposition process that prints gold and ceramic material to create dental appliances available from Optomec Inc. of Albuquerque N. Mex. Other alternative fabrication techniques may also include milling of dental appliance materials and use of electrical discharge machining techniques as are well known in the art.

Figure 12C:
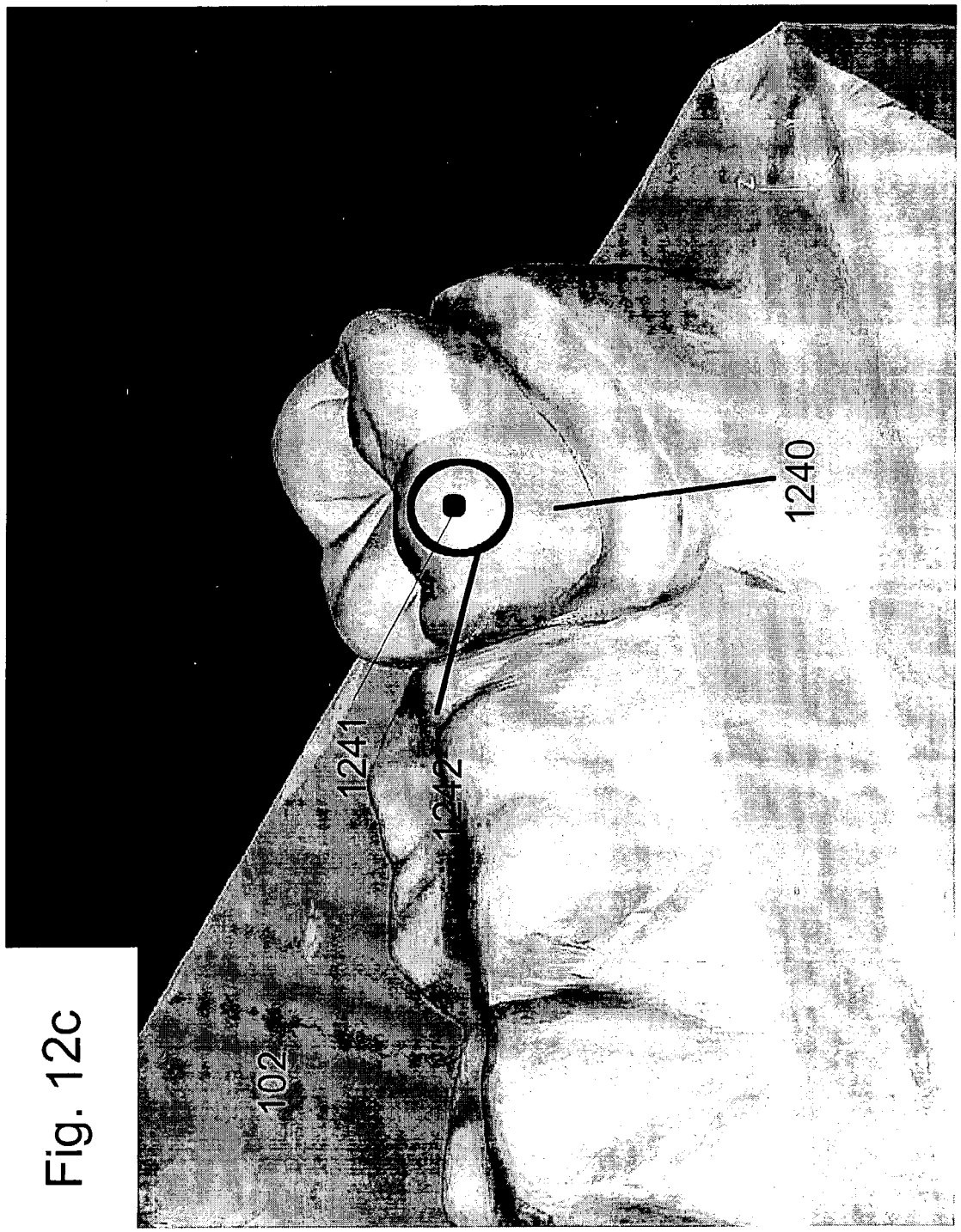

In addition to creating an appliance as described above, the model for the appliance may be manually edited or sculpted once created to define the final definition for the appliance before it is fabricated. This sculpting is performed electronically on the electronic model once created as illustrated in FIG. 12*c*. The surface of the electronic model 1240 is manually moved to change the shape of the application by a dental professional until the desired crown appliance is defined. This process is similar to the manual sculpting of physical models that is well known in the profession.

To alter the surface of the electronic model, the dental professional defines a point on the surface to be moved 1241 and a region of affected surface 1242 on the electronic model. The region of affected surface 1242 is a region of area surrounding the point to be moved 1241. The dental professional then moves the point 1241 to a new location and the processing system alters all of the points on the surface of the electronic model within the region of affective surface 1242 to create a continuous surface and smooth surface between the point being moved 1241 and the remaining surface of the electronic model 1240.

Specifically, the region of affected surface 1242 comprises a circle having a fixed radius located about the point being moved 1241. The amount the surface within the region of affected surface 1242 is moved is determined by a blending function that is applied to points in the region 1242. This blending function may be a cosine function or an exponential function that is scaled over a range of 0 to 1 in which the points nearest to the point being moved 1241 are moved more that the points at the outer radius of the region 1242. The shape of the blending function may be varied to control the contour of the surface within the region of affected area 1242.

As the professional shapes the surface, color mapping of portions of the electronic model may be used to illustrate the proximity of the surfaces of the created appliance with adjacent and opposing teeth surfaces. Additional details regarding the creation and use of color mapping functions is dental electronic models may be found in commonly assigned U.S. Provisional Patent Application Ser. No. 60/376,091 titled "METHOD AND APPARATUS FOR ELECTRONICALLY GENERATING A COLOR DENTAL OCCLUSION MAP WITHIN ELECTRONIC MODEL IMAGES" filed Apr. 29, 2002, which is U.S. patent application titled "METHOD AND APPARATUS FOR ELECTRONICALLY GENERATING A COLOR DENTAL OCCLUSION MAP WITHIN ELECTRONIC MODEL IMAGES", Ser. No. 10/426,252, filed Apr. 29, 2003.

Figure 13:
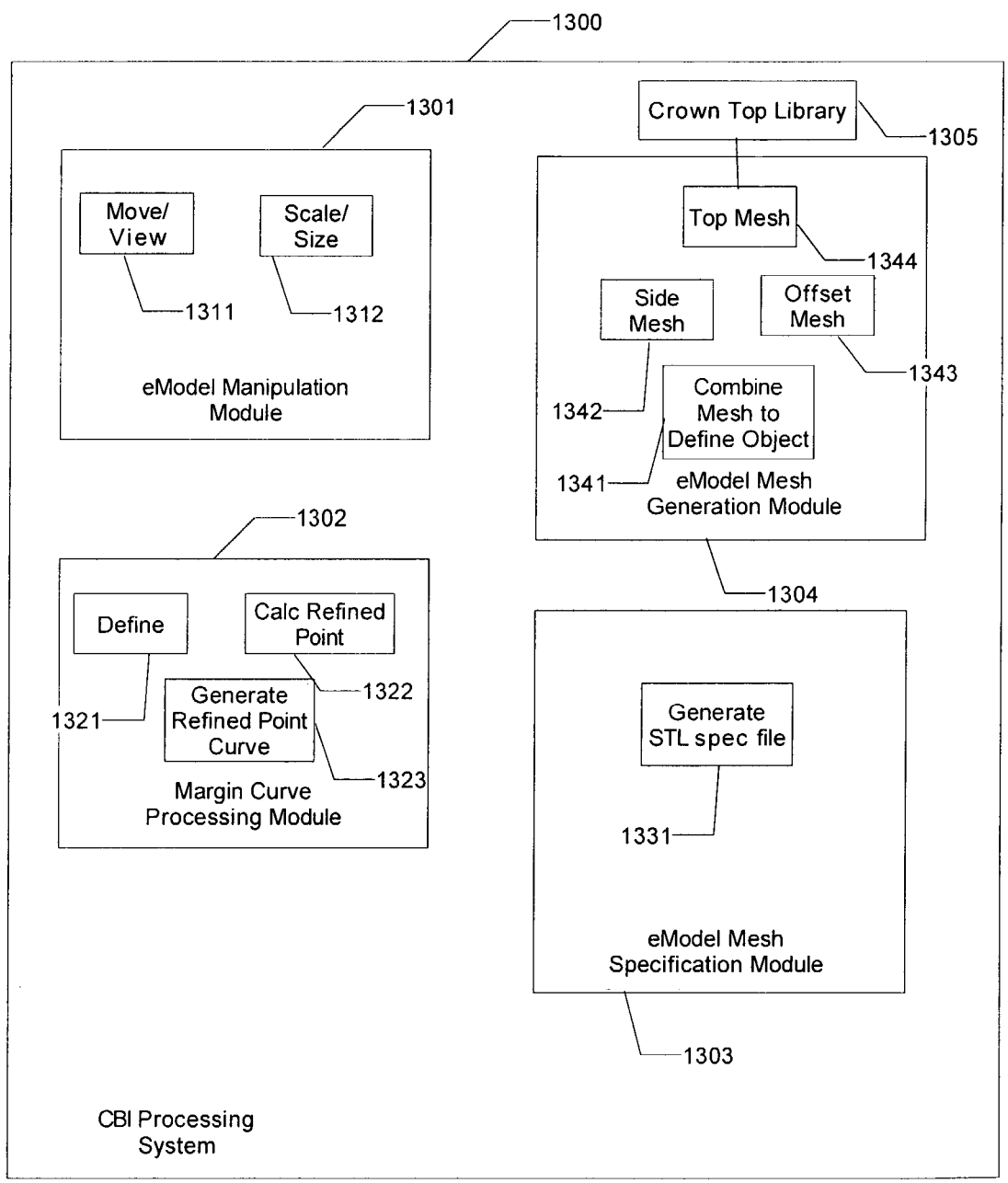
FIG. 13 illustrates a set of processing modules within a CBI processing system utilizes to implement a method for creating dental crowns using a lost-wax manufacturing process from electronic model files corresponding to patient teeth impressions and corresponding electronic models for tooth crowns.

FIG. 13 illustrates a set of processing modules that a CBI processing system utilizes to implement a method for creating dental crowns using a lost-wax manufacturing process from electronic model files corresponding to patient teeth impressions and corresponding electronic models for tooth crowns. A CBI processing system is constructed using an eModel manipulation module 1301, a margin curve processing module 1302, an eModel mesh specification module 1303, an eModel mesh generation module 1304 and a crown top mesh library 1305. These modules, when used together, implement the processes described above.

The eModel manipulation module 1301 permits an operator to manipulate and view various eModel meshes on a computer display device as needed in the above described processing. This module 1301 includes a move and view module 1311 to place and move eModel meshes on a display relative to each other. This module 1301 also includes a scale and size module 1312 to modify the shape of a mesh during the manipulation process.

The margin curve processing module 1302 performs the processing associated with the definition and use of a margin curve that is part of a tooth prep site as needed to define a mesh for the generation of a dental appliance. The margin curve processing module 1302 includes a define module 1321, a calc refine margin point module 1322, and a generate a refined point curve module 1323. The define module 1321 is used by an operator to define the margin curve about a prep site. The calc refine margin point module 1322 is used to generate the refined margin point using the two tangent lines to the mesh surface as discussed above. The generate a refined point curve module 1323 generates a modified mesh surface that moves the margin curve to the refined margin point for all points along the margin curve.

The eModel mesh specification module 1303 contains a generate STL spec file module for processing the internal representation of a mesh defining a dental appliance to generate an output file containing a specification for the appliance that may be made using a rapid prototyping process. As discussed above, the rapid prototyping generates a wax impression that is usable in a lost-wax fabrication process to manufacture the dental appliance.

The eModel mesh generation module 1304 and a crown top mesh library 1305 are used to generate the mesh that specifies the dental appliance. The eModel mesh generation module 1304 includes a top mesh module 1344, a side mesh module 1342, an offset mesh module 1343, and a combine mesh module 1341. The top mesh module 1344 generates the mesh using pre-defined library meshes that are obtained from the crown top mesh library 1305. This mesh is modified in the scale and size module 1312 as needed to fit the patient's prep site.

The side mesh module 1342 generates the side mesh surface from the crown top to the refined margin curve defined in the generate a refined point curve module 1323. The offset mesh module 1343 generates the offset mesh surface that follows the prep site and provides the offset space needed to install the appliance to the prep site. The combine mesh module 1344 stitches the three meshes together into a solid object that is used to generate a specification for the dental appliance in the eModel mesh specification module 1303.

Figure 14:
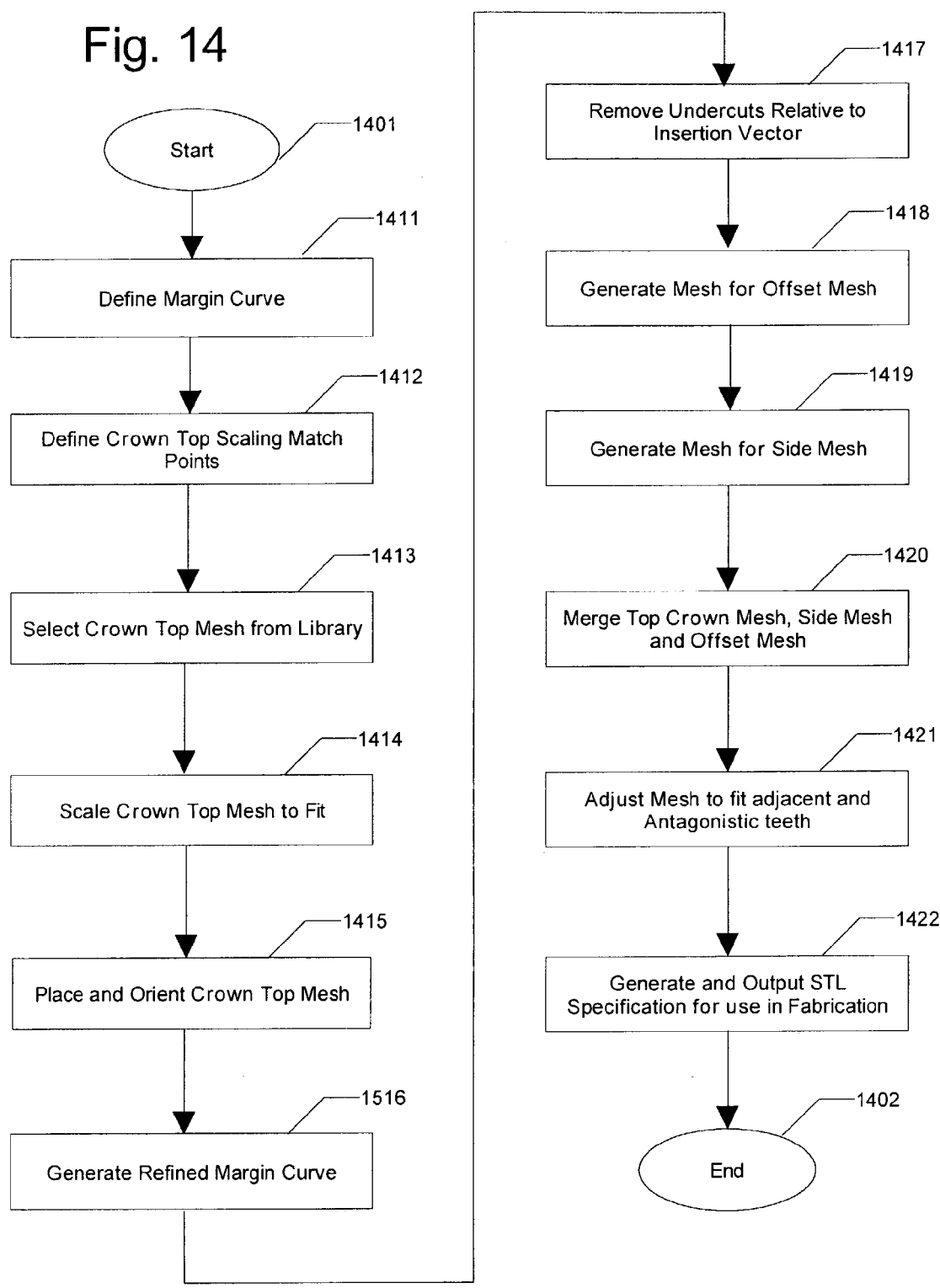
FIG. 14 illustrates an operational flow for a method for creating dental crowns using a lost-wax manufacturing process from electronic model files corresponding to patient teeth impressions and corresponding electronic models for tooth crowns.

FIG. 14 illustrates an operational flow for a method for creating dental crowns using a lost-wax manufacturing process from electronic model files corresponding to patient teeth impressions and corresponding electronic models for tooth crowns. The processing begins 1401 and proceeds to a define margin curve module 1411. The define margin curve module generates a definition for the margin curve around the prep site on an electronic model for the patient's teeth. As discussed above, this curve is used to define the dental appliance's interface to the supporting tooth structure.

The processing then continues with an operator defining the crown top scaling match points in module 1412. As discussed above in reference to FIG. 8, these match points are used to scale a normalized crown top library mesh specification to the size needed for a given patient. The crown top library mesh specification to be used for the dental appliance is selected from the library in module 1413 and then scaled to its proper size in module 1414 using the match points entered in module 1412.

Once the crown is completed, the mesh for the crown top is places upon the prep site in module 1415. The operator manipulates the position and orientation of the crown top mesh as needed to place it into a desired position. This module 1415 also permits an operator to verify the interaction of the crown top mesh with opposing teeth to obtain an optimal placement and orientation.

The margin curve is processed in module 1516 to generate the refined margin curve as discussed above. This refined margin curve provides a more accurate definition for the bottom of the appliance while permitting the proper generation of the offset space between the prep site and the offset mesh. The processing then continues to module 1417 where undercuts in the offset prep site surface are removed relative to the insertion vector expected to be used when the dental appliance is installed onto the prep site.

Once the prep site mesh is corrected, the offset mesh is generated in module 1418. The offset mesh provides a mating surface to the prep site surface with allowance for offset space. This offset space may be a uniform distance of a predetermined value or may be a varying distance depending upon the location within the prep site. In a preferred embodiment, the offset spacing is shown to a dental professional using a color mapping mechanism that illustrates a distance between the inner and outer surfaces using a set of colors. A range of similar distances is illustrated by indicating the distances by superimposing a color from a color map onto the surface of the CBI appliance. A detailed description of the color map process may be found in commonly assigned U.S. Provisional Patent Application titled "METHOD AND APPARATUS FOR ELECTRONICALLY GENERATING A COLOR DENTAL OCCLUSION MAP", Ser. No. 60/376,091, filed Apr. 29, 2002, now U.S. patent application titled "METHOD AND APPARATUS FOR ELECTRONICALLY GENERATING A COLOR DENTAL OCCLUSION MAP", Ser. No. 10/426,252, filed Apr. 29, 2003. These applications are hereby incorporated herein by reference.

Next, the side mesh surfaces are generated between the bottom of the crown top mesh and the refined margin curve in module 1419. This process attempts to define a smooth curved surface. The three meshes, the crown top mesh, the side mesh and the offset mesh are merged together in module 1420 to create a specification for a solid object representing the dental appliance.

Module 1421 is used to permit an operator to adjust the shape of the dental appliance as discussed above with reference to FIG. 12. Similar modifications, if desired may be made to the crown top mesh to correct the interaction of the crown top surface with the opposing tooth. Once the mesh specification for the dental appliance is complete, module 1422 generates an output file containing the dental appliance specification in an STL format. This file is output and the processing ends 1402.

While the above embodiments of the present invention describe a system and method for constructing dental crowns, bridges and implants using a lost-wax process, one skilled in the art will recognize that other methods of manufacture of the dental devices are possible. The present invention allows fabrication of fixed and removable prosthodontic prosthesis such as copings, crowns, inlays, onlays, veneers, bridges, frameworks, implants, abutments, surgical stents, full or partial dentures and other hybrid fixed prosthesis for dental applications. One skilled in the art will easily recognize that other CBI and orthodontic appliances may readily be constructed in accordance of the present invention. As such, long as the manufacturing process utilizes electronic models for impressions of patient's teeth and corresponding electronic models for the crown devices, the present invention to would be useable in other manufacturing methodologies. It is to be understood that other embodiments may be utilized and operational changes may be made without departing from the scope of the present invention.

The foregoing description of the exemplary embodiments of the invention has been presented for the purposes of illustration and description. They are not intended to be exhaustive or to limit the invention to the precise forms disclosed. Many modifications and variations are possible in light of the above teaching. It is intended that the scope of the invention be limited not with this detailed description, but rather by the claims appended hereto. Thus the present invention is presently embodied as a method, apparatus, computer storage medium or propagated signal containing a computer program for providing a method, apparatus, and article of manufacture for constructing dental crowns, bridges and implants.

What is claimed is:

1. A method for constructing a dental appliance for a patient, comprising:
   displaying an electronic model of at least a portion of the teeth of the patient, the displayed portion including a prep site;
   generating a definition for a margin curve around the prep site;
   refining the margin curve;
   creating an electronic model of the dental appliance to be installed on the prep site including;
      selecting a first mesh surface from a library of mush surfaces;
      generating a second mesh surface defined by the refined margin curve; and
      generating a third mesh surface extending between a perimeter of the first mesh surface and the margin curve of the second mesh surface;
   creating an electronic specification from the electronic model; and
   generating a model from the electronic specification using rapid prototyping.

2. The method of claim 1, further comprising fabricating a dental appliance from the wax model using a lost wax process.

3. The method of claim 1, wherein generating the second mesh surface includes generating the second mesh surface with allowance for an offset space between the prep site and the second mesh surface.

4. The method of claim 1, further comprising displaying the electronic model of the dental appliance on the prep site of the displayed portion of the teeth of the patient.

5. The method of claim 1, further comprising:
   defining a set of scaling match points on the margin curve;
   scaling the first mesh surface to a proper size using the set of scaling match points.

6. The method of claim 1, further comprising:
   placing an image of at least one mesh surface on the prep site;
   enabling manipulation of the position and orientation of at least one of the first and third mesh surfaces relative to the prep site to place the mesh surface into a desired position.

7. The method of claim 1, wherein the dental appliance to be created is a crown, a bridge or an implant.

8. The method of claim 1, wherein the displayed portion of the teeth of the patient includes the prep site and at least one tooth adjacent to the prep site.

9. The method of claim 2, wherein the fabricated dental appliance substantially corresponds to the electronic model of the dental appliance.

10. The method of claim 7, wherein the dental appliance to be created is a crown, and the electronic model of the crown is created using a crown top mesh, a crown side mesh, and a crown offset prep mesh.

11. The method of claim 6, further comprising:
    scaling the first mesh surface to a proper size; and
    scaling the third mesh surface to create adequate separation between the dental appliance and/at least one adjacent tooth.

12. The method of claim 6, further comprising scaling the second mesh surface to permit an adhesive to be placed between the prep site and the dental appliance.

13. The method of claim 6, further comprising modifying the shape of the second mesh to eliminate at least one undercut shape in its surface.

14. A processing system for creating at least one dental appliance to be installed onto a prep site, comprising:
    a model manipulation module that allows a user to view, position, scale, and size at least one model polygonal mesh on a computer display;
    a margin curve processing module that generates a refined margin curve;
    a model polygonal mesh generation module configured to generate a polygonal mesh defined by the refined margin curve;
    a model polygonal mesh specification module that generates an output file comprising a specification for a dental appliance, the specification configured for use in a rapid prototyping process; and a library of surfaces that represent occlusal surfaces of teeth known to be within the human mouth.

15. The processing system of claim 14, wherein the library includes electronic polygonal mesh representations of various dental appliances.

16. The processing system of claim 14, wherein the margin curve processing module includes:
    a define module for defining a margin curve around a prep site;
    a cab refine margin point module that generates a refined margin point; and
    a generate reined point curve module;
    wherein the generate reined point curve module generates a modified mesh surface that moves the margin curve to the refined margin point for all points along the margin curve;
    wherein the refined margin points define the refined margin curve.

17. The processing system of claim 14, wherein the model mesh generation module includes;
    a top mesh module that generates or enables selection from the library of a top mesh surface;
    an offset mesh module that generates an offset mesh surface based on the refined margin curve;
    a side mesh module that generates a side mesh surface extending between the refined margin curve and a perimeter of the top mesh surface; and
    a combine mesh module that combines the top mesh, the side mesh, and the offset mesh together to define the final volume for the dental appliance.

18. A method for constructing a dental appliance for a patient, comprising:

displaying an electronic model of at least a portion of the teeth of the patient, the displayed portion including a prep site that requires the dental appliance; and generating a definition for a margin curve around the prep site;

refining the margin curve;

creating an electronic model of the dental appliance to be installed on the prep site, wherein the electronic model of the dental appliance is crested using at least a first, second, and third polygonal mesh that represent different surfaces of the dental appliance to be formed, and wherein the refined margin curve defines the boundaries of one of the polygonal meshes, and wherein creating the electronic model of the dental appliance includes:

selecting a first mesh surface from a library of mesh surfaces;

generating a second mesh surface defined by the margin curve with allowance for an offset space between the prep site and the second mesh surface; and generating a third mesh surface extending between a perimeter of the first mesh surface and the margin curve of the second mesh surface;

creating an electronic specification from the electronic model; and generating a wax model from the electronic specification using rapid prototyping.

* * * * *

UNITED STATES PATENT AND TRADEMARK OFFICE
CERTIFICATE OF CORRECTION

| | | |
|---|---|---|
| PATENT NO. | : 7,228,191 B2 | |
| APPLICATION NO. | : 10/429288 | |
| DATED | : June 5, 2007 | |
| INVENTOR(S) | : Hofmeister et al. | |

It is certified that error appears in the above-identified patent and that said Letters Patent is hereby corrected as shown below:

Col. 3, line 64: "Alomos, N. Mex." should read --Alomos, New Mex.--

Col. 8, line 17: "to the widestpoints across" should read --to the widest points across--

Col. 14, line 45, claim 16: "a cab refine" should read --a calc refine--

Col. 14, line 47, claim 16: "a generated reined point" should read --a generate refined point--

Col. 14, line 48, claim 16: "the generate reined point" should read --the generate refined point--

Signed and Sealed this

Twenty-ninth Day of April, 2008

JON W. DUDAS
*Director of the United States Patent and Trademark Office*